(12) United States Patent
Hinnen et al.

(10) Patent No.: US 6,537,767 B1
(45) Date of Patent: Mar. 25, 2003

(54) METHOD FOR SCREENING ANTIMYCOTICALLY ACTIVE SUBSTANCES

(75) Inventors: Albert Hinnen, Jena (DE); Johannes Hegemann, Düsseldorf (DE); Thomas Munder, Jena (DE); Tillman Schuster, Werneck (DE); Horst Feldmann, München (DE); Wilfried Kramer, Göttingen (DE); Friedrich Karl Zimmermann, Ober-Ramstadt (DE); Karl-Dieter Entian, Oberursel (DE); Matthias Rose, Neu-Anspach (DE); Peter Kötter, Oberursel (DE)

(73) Assignee: Aventis Pharma Deutschland GmbH (DE)

( * ) Notice: Subject to any disclaimer, the term of this patent is extended or adjusted under 35 U.S.C. 154(b) by 0 days.

(21) Appl. No.: 09/402,266
(22) PCT Filed: Apr. 2, 1998
(86) PCT No.: PCT/EP98/01904
§ 371 (c)(1),
(2), (4) Date: Oct. 8, 1999
(87) PCT Pub. No.: WO98/44135
PCT Pub. Date: Oct. 8, 1998

(30) Foreign Application Priority Data

Apr. 2, 1997 (DE) .......................................... 197 13 572

(51) Int. Cl.⁷ ............................................. G01N 33/569
(52) U.S. Cl. ............................ 435/7.31; 435/4; 435/6; 435/7.2; 435/320.1
(58) Field of Search ............................. 435/320.1, 6, 4, 435/7.2, 7.31; 536/23.1

(56) References Cited

U.S. PATENT DOCUMENTS 5,614,377 A    3/1997   Bulawa ........................ 435/32

FOREIGN PATENT DOCUMENTS

| EP | 0 627 491 | 12/1994 |
|----|-----------|---------|
| EP | 0 816 511 | 1/1998 |
| WO | 95/06132  | 3/1995 |
| WO | 95/11969  | 5/1995 |
| WO | 95/34678  | 12/1995 |

OTHER PUBLICATIONS

Gueldener et al., "A New Efficient Gene Disruption Cassette For Repeated Use In Budding Yeast", *Nucleic Acids Research*, vol. 24(13):2519–2524, (1996).

Tuite, "Antifungal Drug Development: The Identification Of New Targets", *Trends In Biotechnology* vol. 10, pp. 235–239, (1992).

Entian et al., "YGR046W, Hypothetical 44.2 kDa Protein; From *S. Cerevisae* Chromosome VII", Database Swiss Prot, Accession No. P53230, Oct. 1, 1996.

Mumberg et al., "Regulatable Promoters Of *Saccharomyces Cerevisiae*: Comparison Of Transcriptional Activity And Their Use For Heterologous Expression", *Nucleic Acids Research*, vol. 22(25):5767–5768, (1994).

*Primary Examiner*—James Ketter
*Assistant Examiner*—Richard Schnizer
(74) *Attorney, Agent, or Firm*—Heller Ehrman White & McAuliffe, LLP

(57) ABSTRACT

The invention relates to a process for screening antimycotically active substances, in which process essential mycete genes, in particular *Saccharomyces cerevisae* genes and functionally homologous and/or sequentially homologous mycete genes, are employed as targets.

A process for finding antimycotically active substances, wherein essential mycete genes are employed as targets.

8 Claims, No Drawings

SEQUENCE LISTING

<160> NUMBER OF SEQ ID NOS: 38

<210> SEQ ID NO 1
<211> LENGTH: 50
<212> TYPE: DNA
<213> ORGANISM: Unknown
<220> FEATURE:
<221> NAME/KEY: misc_feature
<222> LOCATION: (27)..(32)
<223> OTHER INFORMATION: Each n represents a, c, g, or t, and
      collectively represent a suitable cleavage site
<221> NAME/KEY: misc_feature
<222> LOCATION: (27)..(27)
<223> OTHER INFORMATION: n can be a, c, g, or t
<221> NAME/KEY: misc_feature
<222> LOCATION: (28)..(28)
<223> OTHER INFORMATION: n can be a, c, g, or t
<221> NAME/KEY: misc_feature
<222> LOCATION: (29)..(29)
<223> OTHER INFORMATION: n can be a, c, g, or t

```
<221> NAME/KEY: misc_feature
<222> LOCATION: (30)..(30)
<223> OTHER INFORMATION: n can be a, c, g, or t
<221> NAME/KEY: misc_feature
<222> LOCATION: (31)..(31)
<223> OTHER INFORMATION: n can be a, c, g, or t
<221> NAME/KEY: misc_feature
<222> LOCATION: (32)..(32)
<223> OTHER INFORMATION: n can be a, c, g, or t
<221> NAME/KEY: misc_feature
<222> LOCATION: ()..()
<223> OTHER INFORMATION: primer

<400> SEQUENCE: 1
gagagagaga gagagagaga actagtnnnn nntttttttt tttttttttt          50

<210> SEQ ID NO 2
<211> LENGTH: 13
<212> TYPE: DNA
<213> ORGANISM: Unknown
<220> FEATURE:
<221> NAME/KEY: misc_feature
<222> LOCATION: (1)..(5)
<223> OTHER INFORMATION: each n represents a, c, g, or t, and
      collectively represent the cohesive end of a restriction
      cleavage site
<221> NAME/KEY: misc_feature
<222> LOCATION: (1)..(1)
<223> OTHER INFORMATION: n can be a, c, g, or t
<221> NAME/KEY: misc_feature
<222> LOCATION: (2)..(2)
<223> OTHER INFORMATION: n can be a, c, g, or t
<221> NAME/KEY: misc_feature
<222> LOCATION: (3)..(3)
<223> OTHER INFORMATION: n can be a, c, g, or t
<221> NAME/KEY: misc_feature
<222> LOCATION: (4)..(4)
<223> OTHER INFORMATION: n can be a, c, g, or t
<221> NAME/KEY: misc_feature
<222> LOCATION: (5)..(5)
<223> OTHER INFORMATION: n can be a, c, g, or t
<221> NAME/KEY: misc_feature
<222> LOCATION: ()..()
<223> OTHER INFORMATION: primer

<400> SEQUENCE: 2
nnnnnggcac gag                                                   13

<210> SEQ ID NO 3
<211> LENGTH: 24
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 3
gcggccgcaa ggcctccatc gccg                                       24

<210> SEQ ID NO 4
<211> LENGTH: 32
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 4
gatccggcca tggaggcctt gcggccgctg ca                              32
```

<210> SEQ ID NO 5
<211> LENGTH: 37
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 5
atctgcagcg gccgcgtttt aagagcttgg tgagcgc                              37

<210> SEQ ID NO 6
<211> LENGTH: 41
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 6
atggatccgg ccatggaggc ctcgttcaga atgacacgta t                         41

<210> SEQ ID NO 7
<211> LENGTH: 42
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 7
atggatccgg ccatggaggc ctgtgggaat actcaggtat cg                        42

<210> SEQ ID NO 8
<211> LENGTH: 40
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 8
atctgcagcg gccgcgtcta ccctatgaac atattccatt                           40

<210> SEQ ID NO 9
<211> LENGTH: 40
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 9
atctgcagcg gccgcaaaca tgagaattgg gtaataactg                           40

<210> SEQ ID NO 10
<211> LENGTH: 47
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 10
atggatccgg ccatggaggc cttcaagaat tagcttttca attcatc    47

<210> SEQ ID NO 11
<211> LENGTH: 34
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 11
atctgcagcg gccgcattta atagaacagc atcg    34

<210> SEQ ID NO 12
<211> LENGTH: 38
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 12
atggatccgg ccatggaggc cacaccgcat agatcggc    38

<210> SEQ ID NO 13
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 13
aggcagacta caacttagg    19

<210> SEQ ID NO 14
<211> LENGTH: 25
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 14
ctgaattcga tgaggagaag ctagt    25

<210> SEQ ID NO 15
<211> LENGTH: 23
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 15
cttcaaacgc ttgttaaatc ttg    23

<210> SEQ ID NO 16
<211> LENGTH: 25
<212> TYPE: DNA

<213> ORGANISM: Unknown
<220> FEATURE:
<221> NAME/KEY: misc_feature
<222> LOCATION: ()..()
<223> OTHER INFORMATION: primer

<400> SEQUENCE: 16
caggatccgt agaccatttt cagaa                                            25

<210> SEQ ID NO 17
<211> LENGTH: 2973
<212> TYPE: DNA
<213> ORGANISM: Unknown
<220> FEATURE:
<221> NAME/KEY: misc_feature
<222> LOCATION: ()..()
<223> OTHER INFORMATION: Synthetic sequence

<400> SEQUENCE: 17
attgtaagcg ttaatatttt gttaaaattc gcgttaaatt tttgttaaat cagctcattt        60
tttaaccaat aggccgaaat cggcaaaatc ccttataaat caaaagaata gaccgagata       120
gggttgagtc ttgttccagt ttggaacaag agtccactat taaagaacgt ggactccaac       180
gtcaaagggc gaaaaaccgt ctatcagggc gatgcccac tacgtgaacc atcaccctaa        240
tcaagttttt tggggtcgag gtgccgtaaa cgactaaatc ggaaccctaa agggagcccc       300
cgatttagag cttgacgggg aaagccggcg aacgtggcga aaaggaagg gaagaaagcg       360 aaaggagcgg gcgctaggc gctggcaagt gtagcggtca cgctgcgcgt aaccaccaca       420
cccgccgcgc ttaatgctcc gctacagggc gcgtcccatt cgccattcag gctgcgcaac       480
tgttgggaag ggcgatcgt gcgggcctct tcgctattac gccagctggc gaaggggga       540 tgtgctgcaa ggcgattaag ttgggtaacg ccagggtttt cccagtcacg acgttgtaaa       600
acgacggcca gtgagcgcgc gtaatacgac tcactatagg gcgaattgga gctccaccgc       660
ggtggcgctc tagaactagt ggatccggcc atggaggcct gcggccgct gcaggaattc       720 gatatcaagc ttatcgatac cgtcgacctc gagggggggc ccggtaccca gcttttgttc       780
cctttagtga gggttaattg cgcgcttggc gtaatcatgg tcatagctgt ttcctgtgtg       840
aaattgttat ccgctcacaa ttccacacaa catacgagcc ggaagcataa agtgtaaagc       900
ctggggtgcc taatgagtga gctaactcac attaattgcg ttgcgctcac tgcccgcttt       960
ccagtcggga aacctgtcgt gccagctgca ttaatgaatc ggccaacgcg cggggagagg      1020
cggtttgcgt attgggcgct cttccgcttc ctcgctcact gactcgctgc gctcggtcgt      1080
tcggctgcgg cgagcggtat cagctcactc aaaggcggta atacggttat ccacagaatc      1140
aggggataac gcaggaaaga acatgtgagc aaaaggccag caaaaggcca ggaaccgtaa      1200
aaaggccgcg ttgctggcgt ttttccatag gctccgcccc cctgacgagc atcacaaaaa      1260
tcgacgctca agtcagaggt ggcgaaaccc gacaggacta taaagatacc aggcgtttcc      1320
ccctggaagc tccctcgtgc gctctcctgt tccgaccctg ccgcttaccg gatacctgtc      1380
cgcctttctc ccttcgggaa gcgtggcgct ttctcatagc tcacgctgta ggtatctcag      1440
ttcggtgtag tcgttcgct ccaagctggg ctgtgtgcac gaaccccccg ttcagcccga      1500
ccgctgcgcc ttatccggta actatcgtct tgagtccaac ccggtaagac acgacttatc      1560
gccactggca gcagccactg gtaacaggat tagcagagcg aggtatgtag gcggtgctac      1620
agagttcttg aagtggtggc ctaactacgg ctacactaga aggacagtat ttggtatctg      1680
cgctctgctg aagccagtta ccttcggaaa aagagttggt agctcttgat ccggcaaaca      1740

```
aaccaccgct ggtagcggtg gttttttttgt ttgcaagcag cagattacgc gcagaaaaaa       1800
aggatctcaa gaagatcctt tgatcttttc tacggggtct gacgctcagt ggaacgaaaa       1860
ctcacgttaa gggattttgg tcatgagatt atcaaaaagg atcttcacct agatcctttt       1920
aaattaaaaa tgaagtttta aatcaatcta agtatatat gagtaaactt ggtctgacag        1980
ttaccaatgc ttaatcagtg aggcacctat ctcagcgatc tgtctatttc gttcatccat       2040
agttgcctga ctccccgtcg tgtagataac tacgatacgg gagggcttac catctggccc      2100
cagtgctgca atgataccgc gagacccacg ctcaccggct ccagatttat cagcaataaa      2160
ccagccagcc ggaagggccg agcgcagaag tggtcctgca actttatccg cctccatcca      2220
gtctattaat tgttgccggg aagctagagt aagtagttcg ccagttaata gtttgcgcaa      2280
cgttgttgcc attgctacag gcatcgtggt gtcacgctcg tcgtttggta tggcttcatt      2340
cagctccggt tcccaacgat caaggcgagt tacatgatcc cccatgttgt gcaaaaaagc     2400
ggttagctcc ttcggtcctc cgatcgttgt cagaagtaag ttggccgcag tgttatcact      2460
catggttatg gcagcactgc ataattctct tactgtcatg ccatccgtaa gatgcttttc      2520
tgtgactggt gagtactcaa ccaagtcatt ctgagaatag tgtatgcggc gaccgagttg      2580
ctcttgcccg gcgtcaatac gggataatac cgcgccacat agcagaactt aaaagtgct       2640 catcattgga aaacgttctt cggggcgaaa actctcaagg atcttaccgc tgttgagatc      2700
cagttcgatg taacccactc gtgcacccaa ctgatcttca gcatctttta ctttcaccag      2760
cgtttctggg tgagcaaaaa caggaaggca aaatgccgca aaaaagggaa taaggcgac       2820 acggaaatgt tgaatactca tactcttcct ttttcaatat tattgaagca tttatcaggg      2880
ttattgtctc atgagcggat acatatttga atgtatttag aaaaataaac aatagggt       2940 tccgcgcaca tttccccgaa aagtgccacc taa                                    2973
```

<210> SEQ ID NO 18
<211> LENGTH: 4088
<212> TYPE: DNA
<213> ORGANISM: Unknown
<220> FEATURE:
<221> NAME/KEY: misc_feature
<222> LOCATION: ()..()
<223> OTHER INFORMATION: Synthetic sequence

<400> SEQUENCE: 18

```
attgtaagcg ttaatatttt gttaaaattc gcgttaaatt tttgttaaat gacctcattt        60
tttaaccaat aggccgaaat cggcaaaatc ccttataaat caaaagaata gaccgagata      120
gggttgagtg ttgttccagt ttggaacaag agtccactat taaagaacgt ggactccaac      180
gtcaaagggc gaaaaaccgt ctatcagggc gatggcccac tacgtgaacc atcaccctaa     240
tcaagttttt tggggtcgag gtgccgtaaa gcactaaatc ggaaccctaa agggagcccc     300
cgatttagag cttgacgggg aaagccggcg aacgtggcga gaaggaagg gaagaaagcg      360 aaaggagcgg gcgctaggc gctggcaagt gtagcggtca cgctgcgcgt aaccaccaca      420
cccgccgcgc ttaatgcgcc gctacagggc gcgtcccatt cgccattcag gctgcgcaac    480
tgttgggaag ggcgatcggt gcgggcctct tcgctattac gccagctggc gaaggggga      540 tgtgctgcaa ggcgattaag ttgggtaacg ccagggtttt cccagtcacg acgttgtaaa   600
acgacggcca gtgagcgcgc gtaatacgac tcactatagg gcgaattgga gctccaccgc  660
ggtggcgctc tagaactagt ggatccggcc atggaggcct cgttcagaat gacacgtata   720
```

-continued

```
gaatgatgca ttaccttgtc atcttcagta tcatactgtt cgtatacata cttactgaca     780
ttcataggta tacatatata cacatgtata tatatcgtat gctgcagctt taaataatcg     840
gtgtcactac ataagaacac ctttggtgga gggaacatcg ttggtaccat gggcgaggt     900
ggcttctctt atggcaaccg caagagcctt gaacgcactc tcactacggt gatgatcatt     960
cttgcctcgc agacaatcaa cgtggagggt aattctgcta gcctctgcaa agctttcaag    1020
aaaatgcggg atcatctcgc aagagagatc tcctactttc tcccttttgca aaccaagttc    1080
gacaactgcg tacggcctgt tcgaaagatc taccaccgct ctggaaagtg cctcatccaa    1140
aggcgcaaat cctgatccaa acctttttac tccacgcgcc agtagggcct ctttaaaagc    1200
ttgaccgaga gcaatcccgc agtcttcagt ggtgtgatgg tcgtctatgt gtaagtcacc    1260
aatgcactca acgattagcg accagccgga atgcttggcc agagcatgta tcatatggtc    1320
cagaaaccct atacctgtgt ggacgttaat cacttgcgat tgtgtggcct gttctgctac    1380
tgcttctgcc tctttttctg ggaagatcga gtgctctatc gctagggac cacccttttaa    1440
agagatcgca atctgaatct tggtttcatt tgtaatacgc tttactaggg ctttctgctc    1500
tgtcatcttt gccttcgttt atcttgcctg ctcattttt agtatattct tcgaagaaat    1560
cacattactt tatataatgt ataattcatt atgtgataat cggaatcgct aagaaaaaaa    1620
aagagtcatc cgctagggga aaaaaaaaaa tgaaaatcat taccgaggca taaaaaaata    1680
tagagtgtac tagaggaggc caagagtaat agaaaaagaa aattgcggga aaggactgtg    1740
ttatgacttc cctgactaat gccgtgttca acgatacct ggcagtgact cctagcgctc    1800
accaagctct taaaacgcgg ccgctgcagg aattcgatat caagcttatc gataccgtcg    1860
acctcgaggg ggggcccggt acccagcttt tgttcccttt agtgagggtt aattgcgcgc    1920
ttggcgtaat catggtcata gctgtttcct gtgtgaaatt gttatccgct cacaattcca    1980
cacaacatac gagccggaag cataaagtgt aaagcctggg gtgcctaatg agtgagctaa    2040
ctcacattaa ttgcgttgcg ctcactgccc gctttccagt cgggaaacct gtcgtgccag    2100
ctgcattaat gaatcggcca acgcgcgggg agaggcggtt tgcgtattgg gcgctcttcc    2160
gcttcctcgc tcactgactc gctgcgctcg tcgttcggc tgcggcgagc ggtatcagct    2220
cactcaaagg cggtaatacg gttatccaca gaatcagggg ataacgcagg aaagaacatg    2280
tgagcaaaag gccagcaaaa ggccaggaac cgtaaaaagg ccgcgttgct ggcgtttttc    2340
cataggctcc gcccccctga cgagcatcac aaaaatcgac gctcaagtca gaggtggcga    2400
aacccgacag gactataaag ataccaggcg tttccccctg gaagctccct cgtgcgctct    2460
cctgttccga ccctgccgct taccggatac gcgtccgcct tctcccttc gggaagcgtg    2520
gcgctttctc atagctcacg ctgtaggtat ctcagttcgg tgtaggtcgt tcgctccaag    2580
ctgggctgtg tgcacgaacc ccccgttcag cccgaccgct cgccttatc cggtaactat    2640
cgtcttgagt ccaacccggt aagacacgac ttatcgccac tggcagcagc cactggtaac    2700
aggattagca gagcgaggta tgtaggcggt gctacagact tcttgaagtg gtggcctaac    2760
tacggctaca ctagaaggac agtatttggt atctgcgctc tgctgaagcc agttaccttc    2820
ggaaaaagag ttggtagctc ttgatccggc aaagaaacca ccgctggtag cggtggtttt    2880
tttgtttgca agcagcagat tacgcgcaga aaaaaaggat ctcaagaaga tcctttgatc    2940
ttttctacgg ggtctgacgc tcagtggaac gaaaactcac gttaagggat tttggtcatg    3000
agattatcaa aaaggatctt cacctagatc cttttaaatt aaaaatgaag ttttaaatca    3060
atctaaagta tatatgagta aacttggtct gacagttacc aatgcttaat cagtgaggca    3120
```

```
cctatctcag cgatctgtct atttcgttca tccatagttg cctgactccc cgtcgtgtag    3180
ataactacga tacgggaggg cttaccatct ggccccagtg ctgcaatgat accgcgagac    3240
ccacgctcac cggctccaga tttatcagca ataaaccagc cagccggaag ggccgagcgc    3300
agaagtggtc ctgcaacttt atccgcctcc atccagtcta ttaattgttg ccggaagct    3360 agagtaagta gttcgccagt taatagtttg cgcaacgttg ttgccattgc tacaggcatc    3420
gtggtgtcac gctcgtcgtt tggtatggct tcattcagct ccggttccca acgatcaagg    3480
cgagttacat gatcccccat gttgtgcaaa aaagcggtta gctccttcgg tcctccgatc    3540
gttgtcagaa gtaagttggc cgcagtgtta tcactcatgg ttatggcagc actgcataat    3600
tctcttactg tcatgccatc cgtaagatcg ttttctgtga ctggtgagta ctcaaccaag    3660
tcattctgag aatagtgtat gcggcgaccg agttgctctt gcccggcgtc aatacgggat    3720
aataccgcgc cacatagcag aactttaaaa gtgctcatca ttggaaaacg ttcttcgggg    3780
cgaaaactct caaggatctt accgctgttg agatccagtt cgatgtaacc cactcgtgca    3840
cccaactgat cttcagcatc ttttactttc accagcgttt ctgggtgagc aaaaacagga    3900
aggcaaaatg ccgcaaaaaa gggaataagg gcgacacgga aatgttgaat actcatactc    3960
ttcctttttc aatattattg aagcatttat cagggttatt gtctcatgag cggatacata    4020
tttgaatgta tttagaaaaa taaacaaata ggggttccgc gcacatttcc ccgaaaagtg    4080
ccacctaa                                                            4088
```

<210> SEQ ID NO 19
<211> LENGTH: 4583
<212> TYPE: DNA
<213> ORGANISM: Unknown
<220> FEATURE:
<221> NAME/KEY: misc_feature
<222> LOCATION: ()..()
<223> OTHER INFORMATION: Synthetic sequence

<400> SEQUENCE: 19

```
attgtaagcg ttaatatttt gttaaaattc gcgttaaatt tttgttaaat cagctcattt     60
tttaaccaat aggccgaaat cggcaaaatc ccttataaat caaaagaata gaccgagata    120
gggttgagtg ttgttccagt ttggaacaag agtccactat taaagaacgt ggactccaac    180
gtcaaagggc gaaaaaccgt ctatcagggc gatggcccac tacgtgaacc atcaccctaa    240
tcaagttttt tggggtcgag gtgccgtaaa gcactaaatc ggaaccctaa agggagcccc    300
cgatttagag cttgacgggg aaagccggcg aacgtggcga gaaaggaagg gaagaaagcg    360
aaaggagcgg cgctagggc gctggcaagt gtagcggtca cgctgcgcgt aaccaccaca    420
cccgccgcgc ttaatgcgcc gctacagggc gcgtcccatt cgccattcag ctgcgcaac    480 tgttgggaag ggcgatcgt gcgggcctct tcgctattac gccagctggc gaaggggga    540 tgtgctgcaa ggcgattaag ttgggtaacg ccagggtttt cccagtcacg acgttgtaaa    600
acgacggcca gtgagcgcgc gtaatacgac tcactatagg gcgaattgga gctccaccgc    660
ggtggcgctc tagaactagt ggatccggcc atggaggcct gtgggaatac tcaggtatcg    720
taagatgcaa gagttcgaat ctcttagcaa ccattatttt tttcctcaac ataacgagaa    780
cacacagggg cgctatcgca cagaatcaaa ttcgatgact ggaaattttt tgttaatttc    840
agaggtcgcc tgacgcatat accttttca actgaaaaat tgggagaaaa aggaaaggtg    900
agaggccgga accggctttt catatagaat agagaagcgt tcatgactaa atgcttgcat    960
```

| | |
|---|---|
| cacaatactt gaagttgaca atattattta aggacctatt gttttttcca ataggtggtt | 1020 |
| agcaatcgtc ttactttcta acttttctta ccttttacat ttcagcaata tatatatata | 1080 |
| tttcaaggat ataccattct aatgtctgcc cctatgtctg ccctaagaa gatcgtcgtt | 1140 |
| ttgccaggtg accacgttgg tcaagaaatc acagccgaag ccattaaggt tcttaaagct | 1200 |
| atttctgatt ttcgttccaa tgtcaagttc gatttcgaaa atcatttaat tggtggtgct | 1260 |
| gctatcgatg ctacaggtgt cccacttcca gatgaggcgc tggaagcctc caagaaggtt | 1320 |
| gatgccgttt tgttaggtgc tgtgggtggt cctaaatggg gtacaggtag tgttagacct | 1380 |
| gaacaaggtt tactaaaaat ccgtaaagaa cttcaattgt acgccaactt aagaccatgt | 1440 |
| aactttgcat ccgactctct tttagactta tctccaatca agccacaatt tgctaaaggt | 1500 |
| actgacttcg ttgttgtcag agaattagtg ggaggtattt actttggtaa gagaaaggaa | 1560 |
| gacgatggtg atggtgtcgc ttgggatagt gaacaataca ccgttccaga agtgcaaaga | 1620 |
| atcacaagaa tggccgcttt catggcccta caacatgacc caccattgcc tatttggtcc | 1680 |
| ttggataaag ctaatgtttt ggcctcttca agattatgga gaaaaactgt ggaggaaacc | 1740 |
| atcaagaacg aatttcctac attgaaggtt caacatcaat tgattgattc tgccgccatg | 1800 |
| atcctagtta agaacccaac ccacctaaat ggtattataa tcaccagcaa catgtttggt | 1860 |
| gatatcatct ccgatgaagc ctccgttatc ccaggttcct gggtttgtt gccatctgcg | 1920 |
| tccttggcct ctttgccaga caagaacacc gcatttggtt tgtacgaacc atgccacggt | 1980 |
| tctgctccag atttgccaaa gaataaggtt gaccctatcg ccactatctt gtctgctgca | 2040 |
| atgatgttga aattgtcatt gaacttgcct gaagaaggta aggccattga agatgcagtt | 2100 |
| aaaaaggttt tggatgcagg tatcagaact ggtgatttag gtggttccaa cagtaccacc | 2160 |
| gaagtcggtg atgctgtcgc cgaagaagtt aagaaaatcc ttgcttaaaa agattctctt | 2220 |
| tttttatgat atttgtacat aaactttata aatgaaattc ataatagaaa cgacacgaaa | 2280 |
| ttacaaaatg gaatatgttc atagggtaga cgcggccgct gcaggaattc gatatcaagc | 2340 |
| ttatcgatac cgtcgacctc gagggggggc ccggtaccca gcttttgttc cctttagtga | 2400 |
| gggttaattg cgcgcttggc gtaatcatgg tcatagctgt ttcctgtgtg aaattgttat | 2460 |
| ccgctcacaa ttccacacaa catacgagcc ggaagcataa agtgtaaagc ctggggtgcc | 2520 |
| taatgagtga gctaactcac attaattgcg ttgcgctcac tgcccgcttt ccagtcggga | 2580 |
| aacctgtcgt gccagctgca ttaatgaatc ggccaacgcg cggggagagg cggtttgcgt | 2640 |
| attgggcgct cttccgcttc ctcgctcact gactcgctgc gctcggtcgt tcggctgcgg | 2700 |
| cgagcggtat cagctcactc aaaggcggta atacggttat ccacagaatc aggggataac | 2760 |
| gcaggaaaga acatgtgagc aaaaggccag caaaaggcca ggaaccgtaa aaaggccgcg | 2820 |
| ttgctggcgt ttttccatag gctccgcccc cctgacgagc atcacaaaaa tcgacgctca | 2880 |
| agtcagaggt ggcgaaaccc gacaggacta taaagatacc aggcgtttcc ccctggaagc | 2940 |
| tccctcgtgc gctctcctgt tccgaccctg ccgcttaccg gatacctgtc cgcctttctc | 3000 |
| ccttcgggaa gcgtggcgct ttctcatagc tcacgctgta ggtatctcag ttcggtgtag | 3060 |
| gtcgttcgct ccaagctggg ctgtgtgcac gaaccccccg ttcagcccga ccgctgcgcc | 3120 |
| ttatccggta actatcgtct tgagtccaac ccggtaagac acgacttatc gccactggca | 3180 |
| gcagccactg gtaacaggat tagcagagcg aggtatgtag cggtgctac agagttcttg | 3240 |
| aagtggtggc ctaactacgg ctacactaga aggacagtat ttggtatctg cgctctgctg | 3300 |
| aagccagtta ccttcggaaa aagagttggt agctcttgat ccggcaaaca aaccaccgct | 3360 |

-continued

```
ggtagcggtg gttttttttgt ttgcaagcag cagattacgc gcagaaaaaa aggatctcaa      3420
gaagatcctt tgatcttttc tacggggtct gacgctcagt ggaacgaaaa ctcacgttaa      3480
gggattttgg tcatgagatt atcaaaaagg atcttcacct agatccttt aaattaaaaa       3540
tgaagttttta aatcaatcta agtatatat gagtaaactt ggtctgacag ttaccaatgc      3600
ttaatcagtg aggcacctat ctcagcgatc tgtctatttc gttcatccat agttgcctga      3660
ctccccgtcg tgtagataac tacgatacgg gagggcttac catctggccc cagtgctgca     3720
atgataccgc gagacccacg ctcaccggct ccagatttat cagcaataaa ccagccagcc     3780
ggaagggccg agcgcagaag tggtcctgca actttatccg cctccatcca gtctattaat    3840
tgttgccggg aagctagagt aagtagttcg ccagttaata gtttgcgcaa cgttgttgcc    3900
attgctacag gcatcgtggt gtcacgctcg tcgtttggta tggcttcatt cagctccggt   3960
tcccaacgat caaggcgagt tacatgatcc cccatgttgt gcaaaaaagc ggttagctcc    4020
ttcggtcctc cgatcgttgt cagaagtaag ttggccgcag tgttatcact catggttatg   4080
gcagcactgc ataattctct tactgtcatg ccatccgtaa gatgcttttc tgtgactggt   4140
gagtactcaa ccaagtcatt ctgagaatag tgtatgcggc gaccgagttg ctcttgcccg   4200
gcgtcaatac gggataatac cgcgccacat agcagaactt taaaagtgct catcattgga   4260
aaacgttctt cggggcgaaa actctcaagg atcttaccgc tgttgagatc cagttcgatg   4320
taacccactc gtgcacccaa ctgatcttca gcatctttta ctttcaccag cgtttctggg   4380
tgagcaaaaa caggaaggca aaatgccgca aaaaagggaa taagggcgac acggaaatgt   4440
tgaatactca tactcttcct ttttcaatat tattgaagca tttatcaggg ttattgtctc   4500
atgagcggat acatatttga atgtatttag aaaaataaac aatagggt ccgcgcaca     4560
tttccccgaa aagtgccacc taa                                              4583
```

<210> SEQ ID NO 20
<211> LENGTH: 4102
<212> TYPE: DNA
<213> ORGANISM: Unknown
<220> FEATURE:
<221> NAME/KEY: misc_feature
<222> LOCATION: ()..()
<223> OTHER INFORMATION: Synthetic sequence

<400> SEQUENCE: 20

```
attgtaagcg ttaatatttt gttaaaattc gcgttaaatt tttgttaaat cagctcattt       60
tttaaccaat aggccgaaat cggcaaaatc ccttataaat caaaagaata gaccgagata      120
gggttgagtg ttgttccagt ttggaacaag agtccactat taaagaacgt ggactccaac      180
gtcaaagggc gaaaaaccgt ctatcagggc gatggcccac tacgtgaacc atcaccctaa     240
tcaagttttt tggggtcgag gtgccgtaaa gcactaaatc ggaaccctaa agggagcccc      300
cgatttagag cttgacgggg aaagccggcg aacgtggcga aaaggaagg gaagaaagcg      360
aaaggagcgg gcgctaggc gctggcaagt gtagcggtca cgctgcgcgt aaccaccaca     420
cccgccgcgc ttaatgcgcc gctacagggc gcgtcccatt cgccattcag ctgcgcaac      480
tgttgggaag ggcgatcgt gcgggcctct tcgctattac gccagctggc gaaggggga      540
tgtgctgcaa ggcgattaag ttgggtaacg ccagggtttt cccagtcacg acgttgtaaa    600
acgacggcca gtgagcgcgc gtaatacgac tcactatagg gcgaattgga gctccaccgc    660
ggtggcgctc tagaactagt ggatccggcc atggaggcct tcaagaatta gcttttcaat    720
```

-continued

```
tcaattcatc atttttttt tattcttttt tttgatttcg gtttctttga aatttttttg      780
attcggtaat ctccgaacag aaggaagaac gaaggaagga gcacagactt agattggtat      840
atatacgcat atgtagtgtt gaagaaacat gaaattgccc agtattctta acccaactgc      900
acagaacaaa aacatgcagg aaacgaagat aaatcatgtc gaaagctaca tataaggaac      960
gtgctgctac tcatcctagt cctgttgctg ccaagctatt taatatcatg cacgaaaagc     1020
aaacaaactt gtgtgcttca ttggatgttc gtaccaccaa ggaattactg gagttagttg     1080
aagcattagg tcccaaaatt tgtttactaa aacacatgt ggatatcttg actgattttt      1140
ccatggaggg cacagttaag ccgctaaagg cattatccgc caagtacaat tttttactct     1200
tcgaagacag aaaatttgct gacattggta atacagtcaa attgcagtac tctgcgggtg     1260
tatacagaat agcagaatgg gcagacatta cgaatgcaca cggtgtggtg ggcccaggta     1320
ttgttagcgg tttgaagcag gcggcagaag aagtaacaaa ggaacctaga ggccttttga     1380
tgttagcaga attgtcatgc aagggctccc tatctactgg agaatatact aagggtactg     1440
ttgacattgc gaagagcgac aaagattttg ttatcggctt tattgctcaa agagacatgg     1500
gtggaagaga tgaaggttac gattggttga ttatgacacc cggtgtgggt ttagatgaca     1560
agggagacgc attgggtcaa cagtatagaa ccgtggatga tgtggtctct acaggatctg     1620
acattattat tgttggaaga ggactatttg caaagggaag ggatgctaag gtagagggtg     1680
aacgttacag aaaagcaggc tgggaagcat atttgagaag atgcggccag caaaactaaa     1740
aaactgtatt ataagtaaat gcatgtatac taaactcaca aattagagct tcaatttaat     1800
tatatcagtt attacccaat tctcatgttt gcggccgctg caggaattcg atatcaagct     1860
tatcgatacc gtcgacctcg agggggggcc cggtacccca cttttgttcc ctttagtgag     1920
ggttaattgc gcgcttggcg taatcatggt catagctgtt tcctgtgtga aattgttatc     1980
cgctcacaat tccacacaac atacgagccg aagcataaa gtgtaaagcc tggggtgcct     2040
aatgagtgag ctaactcaca ttaattgcgt tgcgctcact gcccgctttc cagtcgggaa     2100
acctgtcgtg ccagctgcat taatgaatcg gccaacgcgc ggggagaggc ggtttgcgta     2160
ttgggcgctc ttccgcttcc tcgctcactg actcgctgcg ctcggtcgtt cggctgcggc     2220
gagcggtatc agctcactca aaggcggtaa tacggttatc cacagaatca ggggataacg     2280
caggaaagaa catgtgagca aaaggccagc aaaaggccag gaaccgtaaa aaggccgcgt     2340
tgctggcgtt tttccatagg ctccgccccc ctgacgagca tcacaaaaat cgacgctcaa     2400
gtcagaggtg gcgaaacccg acaggactat aaagatacca ggcgtttccc cctggaagct     2460
ccctcgtgcg ctctcctgtt ccgacccctgc cgcttaccgg atacctgtcc gcctttctcc     2520
cttcgggaag cgtggcgctt tctcatagct cacgctgtag gtatctcagt tcggtgtagg     2580
tcgttcgctc caagctgggc tgtgtgcacg aaccccccgt tcagcccgac cgctgcgcct     2640
tatccggtaa ctatcgtctt gagtccaacc cggtaagaca cgacttatcg ccactggcag     2700
cagccactgg taacaggatt agcagagcga ggtatgtagg cggtgctaca gagttcttga     2760
agtggtggcc taactacggc tacactagaa ggacagtatt tggtatctgc gctctgctga     2820
agccagttac cttcggaaaa agagttggta gctcttgatc cggcaaacaa accaccgctg     2880
gtagcggtgg ttttttttgtt tgcaagcagc agattacgcg cagaaaaaaa ggatctcaag     2940
aagatccttt gatcttttct acggggtctg acgctcagtg gaacgaaaac tcacgttaag     3000 ggatttttggt catgagatta tcaaaaagga tcttcaccta gatcctttta aattaaaaat     3060
gaagttttaa atcaatctaa agtatatatg agtaaacttg gtctgacagt taccaatgct     3120
```

-continued

```
taatcagtga ggcacctatc tcagcgatct gtctatttcg ttcatccata gttgcctgac    3180
tccccgtcgt gtagataact acgatacggg agggcttacc atctggcccc agtgctgcaa    3240
tgataccgcg agacccacgc tcaccggctc cagatttatc agcaataaac cagccagccg    3300
gaagggccga gcgcagaagt ggtcctgcaa ctttatccgc ctccatccag tctattaatt    3360
gttgccggga agctagagta agtagttcgc cagttaatag tttgcgcaac gttgttgcca    3420
ttgctacagg catcgtggtg tcacgctcgt cgtttggtat ggcttcattc agctccggtt    3480
cccaacgatc aaggcgagtt acatgatccc ccatgttgtg caaaaaagcg gttagctcct    3540
tcggtcctcc gatcgttgtc agaagtaagt tggccgcagt gttatcactc atggttatgg    3600
cagcactgca taattctctt actgtcatgc catccgtaag atgcttttct gtgactggtg    3660
agtactcaac caagtcattc tgagaatagt gtatgcggcg accgagttgc tcttgcccgg    3720
cgtcaatacg ggataatacc gcgccacata gcagaacttt aaaagtgctc atcattggaa    3780
aacgttcttc ggggcgaaaa ctctcaagga tcttaccgct gttgagatcc agttcgatgt    3840
aacccactcg tgcacccaac tgatcttcag catcttttac tttcaccagc gtttctgggt    3900
gagcaaaaac aggaaggcaa aatgccgcaa aaagggaat aagggcgaca cggaaatgtt    3960
gaatactcat actcttcctt tttcaatatt attgaagcat ttatcagggt tattgtctca    4020
tgagcggata catatttgaa tgtatttaga aaataaaca aatagggggtt ccgcgcacat    4080 ttccccgaaa agtgccacct aa                                              4102
```

<210> SEQ ID NO 21
<211> LENGTH: 3956
<212> TYPE: DNA
<213> ORGANISM: Unknown
<220> FEATURE:
<221> NAME/KEY: misc_feature
<222> LOCATION: ()..()
<223> OTHER INFORMATION: Synthetic sequence

<400> SEQUENCE: 21

```
attgtaagcg ttaatatttt gttaaaattc gcgttaaatt tttgttaaat cagctcattt      60
tttaaccaat aggccgaaat cggcaaaatc ccttataaat caaaagaata gaccgagata     120
gggttgagtg ttgttccagt ttggaacaag agtccactat taaagaacgt ggactccaac     180
gtcaaagggc gaaaaaccgt ctatcagggc gatggcccac tacgtgaacc atcaccctaa     240
tcaagttttt tggggtcgag gtgccgtaaa gcactaaatc ggaaccctaa agggagcccc     300
cgatttagag cttgacgggg aaagccggcg aacgtggcga gaaaggaagg gaagaaagcg     360
aaaggagcgg gcgctagggc gctggcaagt gtagcggtca cgctgcgcgt aaccaccaca     420
cccgccgcgc ttaatgcgcc gctacagggc gcgtcccatt cgccattcag ctgcgcaac     480 tgttgggaag ggcgatcgt gcgggcctct tcgctattac gccagctggc gaagggggga     540
tgtgctgcaa ggcgattaag ttgggtaacg ccagggtttt cccagtcacg acgttgtaaa     600
acgacggcca gtgagcgcgc gtaatacgac tcactatagg gcgaattgga gctccaccgc     660
ggtggcgctc tagaactagt ggatccggcc atggaggcca caccgcatag atcggcaagt     720
gcacaaacaa tacttaaata aatactactc agtaataacc tatttcttag cattttttgac    780 gaaatttgct attttgttag agtctttttac accatttgtc tccacacctc cgcttacatc     840
aacaccaata acgccattta atctaagcgc atcaccaaca ttttctggcg tcagtccacc     900
agctaacata aaatgtaagc tttcggggct ctcttgcctt ccaacccagt cagaaatcga     960
```

```
gttccaatcc aaaagttcac ctgtcccacc tgcttctgaa tcaaacaagg gaataaacga     1020
atgaggtttc tgtgaagctg cactgagtag tatgttgcag tcttttggaa atacgagtct     1080
tttaataact ggcaaaccga ggaactcttg gtattcttgc cacgactcat ctccatgcag     1140
ttggacgata tcaatgccgt aatcattgac cagagccaaa acatcctcct taggttgatt     1200
acgaaacacg ccaaccaagt atttcggagt gcctgaacta tttttatatg cttttacaag     1260
acttgaaatt ttccttgcaa taaccgggtc aattgttctc tttctattgg gcacacatat     1320
aatacccagc aagtcagcat cggaatctag agcacattct gcggcctctg tgctctgcaa     1380 gccgcaaaact ttcaccaatg gaccagaact acctgtgaaa ttaataacag acatactcca     1440
agctgccttt gtgtgcttaa tcacgtatac tcacgtgctc aatagtcacc aatgccctcc     1500
ctcttggccc tctccttttc tttttttcgac cgaattaatt cttaatcggc aaaaaaagaa     1560
aagctccgga tcaagattgt acgtaaggta caagctatt tttcaataaa gaatatcttc       1620
cactactgcc atctggcgtc ataactgcaa agtacacata tattacgatg ctgttctatt     1680
aaatgcggcc gctgcaggaa ttcgatatca agcttatcga taccgtcgac ctcgaggggg     1740
ggcccggtac ccagctttg ttccctttag tgagggttaa ttgcgcgctt ggcgtaatca      1800
tggtcatagc tgtttcctgt gtgaaattgt tatccgctca caattccaca caacatacga     1860 gccgaagca taaagtgtaa agcctggggt gcctaatgag tgagctaact cacattaatt      1920
gcgttgcgct cactgcccgc tttccagtcg ggaaacctgt cgtgccagct gcattaatga     1980
atcggccaac gcgcggggag aggcggtttg cgtattgggc gctcttccgc ttcctcgctc     2040
actgactcgc tgcgctcggt cgttcggctg cggcgagcgg tatcagctca ctcaaaggcg     2100
gtaatacggt tatccacaga atcaggggat aacgcaggaa agaacatgtg agcaaaaggc     2160
cagcaaaagg ccaggaaccg taaaaaggcc gcgttgctgg cgtttttcca taggctccgc     2220
ccccctgacg agcatcacaa aaatcgacgc tcaagtcaga ggtggcgaaa cccgacagga     2280
ctataaagat accaggcgtt tcccctgga agctccctcg tgcgctctcc tgttccgacc     2340
ctgccgctta ccggatacct gtccgccttt ctcccttcgg gaagcgtggc gctttctcat     2400
agctcacgct gtaggtatct cagttcggtg taggtcgttc gctccaagct gggctgtgtg     2460
cacgaacccc ccgttcagcc cgaccgctgc gccttatccg gtaactatcg tcttgagtcc     2520
aacccggtaa gacacgactt atcgccactg gcagcagcca ctggtaacag gattagcaga     2580
gcgaggtatg taggcggtgc tacagagttc ttgaagtggt ggcctaacta cggctacact     2640
agaaggacag tatttggtat ctgcgctctg ctgaagccag ttaccttcgg aaaaagagtt     2700
ggtagctctt gatccggcaa acaaaccacc gctggtagcg gtggtttttt tgtttgcaag     2760
cagcagatta cgcgcagaaa aaaggatctc aagaagatc ctttgatctt ttctacgggg      2820
tctgacgctc agtggaacga aaactcacgt taagggattt tggtcatgag attatcaaaa     2880
aggatcttca cctagatcct tttaaattaa aaatgaagtt ttaaatcaat ctaaagtata     2940
tatgagtaaa cttggtctga cagttaccaa tgcttaatca gtgaggcacc tatctcagcg     3000
atctgtctat ttcgttcatc catagttgcc tgactccccg tcgtgtagat aactacgata     3060
cgggagggct taccatctgg ccccagtgct gcaatgatac cgcgagaccc acgctcaccg     3120
gctccagatt tatcagcaat aaaccagcca gccggaaggg ccgagcgcag aagtggtcct     3180
gcaactttat ccgcctccat ccagtctatt aattgttgcc gggaagctag agtaagtagt     3240
tcgccagtta atagtttgcg caacgttgtt gccattgcta caggcatcgt ggtgtcacgc     3300
tcgtcgtttg gtatggcttc attcagctcc ggttcccaac gatcaaggcg agttacatga     3360
```

```
tcccccatgt tgtgcaaaaa agcggttagc tccttcggtc ctccgatcgt tgtcagaagt      3420
aagttggccg cagtgttatc actcatggtt atggcagcac tgcataattc tcttactgtc      3480
atgccatccg taagatgctt ttctgtgact ggtgagtact caaccaagtc attctgagaa      3540
tagtgtatgc ggcgaccgag ttgctcttgc ccggcgtcaa tacgggataa taccgcgcca      3600
catagcagaa ctttaaaagt gctcatcatt ggaaaacgtt cttcggggcg aaaactctca      3660
aggatcttac cgctgttgag atccagttcg atgtaaccca ctcgtgcacc caactgatct      3720
tcagcatctt ttactttcac cagcgtttct gggtgagcaa aaacaggaag gcaaaatgcc      3780
gcaaaaaagg gaataagggc gacacggaaa tgttgaatac tcatactctt ccttttcaa      3840 tattattgaa gcatttatca gggttattgt ctcatgagcg gatacatatt tgaatgtatt      3900
tagaaaaata aacaaatagg ggttccgcgc acatttcccc gaaaagtgcc acctaa         3956
```

<210> SEQ ID NO 22
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 22
ataggcgctt ctcgtatcta tactcaaccc gcccccaatg cagctgaagc ttcgtacgc       59

<210> SEQ ID NO 23
<211> LENGTH: 60
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 23
aaattggggg cacaaatgag gggtaaaaat gcagacatta gcataggcca ctagtggatc      60

<210> SEQ ID NO 24
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 24
tctaaatcgt tatgttgaaa acctaggcac caatgtgact cagctgaagc ttcgtacgc       59

<210> SEQ ID NO 25
<211> LENGTH: 60
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 25
cagcttttgc ccaatatgct caaaaccgag ttatctatta gcataggcca ctagtggatc      60

<210> SEQ ID NO 26

```
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 26
caagttactt tgaaaggaaa taaaaaaat tgtcagcatg cagctgaagc ttcgtacgc      59

<210> SEQ ID NO 27
<211> LENGTH: 60
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 27
atatttgatg caatttctgc cttaaagtac aaaatgctta gcataggcca ctagtggatc    60

<210> SEQ ID NO 28
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 28
aatattcata aaacaggatc tttcaaggga cgataaaatg cagctgaagc ttcgtacgc     59

<210> SEQ ID NO 29
<211> LENGTH: 62
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 29
ttcctatttt attgtacaaa atgcgcgact attccgttta gcataggcca ctagtggatc    60
tg                                                                  62

<210> SEQ ID NO 30
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 30
tcaatcgaag catttgaagc atactctaga ccaaagaaga cagctgaagc ttcgtacgc     59

<210> SEQ ID NO 31
<211> LENGTH: 62
<212> TYPE: DNA
<213> ORGANISM: Unknown
<220> FEATURE:
<221> NAME/KEY: misc_feature
<222> LOCATION: ()..()
<223> OTHER INFORMATION: primer
```

<400> SEQUENCE: 31
ttgaattcaa gacaaaaaat caaatcttgc tgagttgtta gcataggcca ctagtggatc    60
tg    62

<210> SEQ ID NO 32
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 32
gaagcctggc tataccaatc cggctttaaa agcccttggt cagctgaagc ttcgtacgc    59

<210> SEQ ID NO 33
<211> LENGTH: 62
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 33
ctttaccctg tttgacccag ttctgtggcc aatcttttc gcataggcca ctagtggatc    60
tg    62

<210> SEQ ID NO 34
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 34
ttcctaaaag taattcttaa aagtgataat gaatgactta cagctgaagc ttcgtacgc    59

<210> SEQ ID NO 35
<211> LENGTH: 62
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 35
acctagttga aaagatttgt tccgcagata agaaaaaatg gcataggcca ctagtggatc    60
tg    62

<210> SEQ ID NO 36
<211> LENGTH: 59
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 36

```
cacagggccg cattatttct ttgatttcgt tttttcacc cagctgaagc ttcgtacgc        59

<210> SEQ ID NO 37
<211> LENGTH: 62
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 37
gatttagaga ttcaaactcc gttattttta gaaggtcatg gcataggcca ctagtggatc        60
tg                                                                      62

<210> SEQ ID NO 38
<211> LENGTH: 9
<212> TYPE: DNA
<213> ORGANISM: Unknown
<220> FEATURE:
<221> NAME/KEY: misc_feature
<222> LOCATION: (1)..(1)
<223> OTHER INFORMATION: "n" constitutes the cohesive end of a
      restriction cleavage site
<221> NAME/KEY: misc_feature
<222> LOCATION: (1)..(1)
<223> OTHER INFORMATION: n can be a, c, g, or t
<221> NAME/KEY: misc_feature
<222> LOCATION: ()..()
<223> OTHER INFORMATION: primer

<400> SEQUENCE: 38 nccgtgctc                                                               9
```

METHOD FOR SCREENING ANTIMYCOTICALLY ACTIVE SUBSTANCES

The invention relates to a process for screening antimycotically active substances, in which process essential genes from mycetes, in particular *Saccharomyces cerevisiae*, as well as mycete genes which are homologous with regard to function and/or sequence, are employed as targets.

The spectrum of known fungal infections extends all the way from fungal infestations of the skin surface or the nails to potentially life-threatening mycotic infections of the internal organs. Infections of this nature, and the sequelae which accompany them, are termed mycoses.

Antimycotically (fungistatically or fungicidally) active substances are employed for treating mycoses. However, only relatively few pharmacologically active substances, such as amphotericin B, nystatin, pimaricin, griseofulvin, clotrimazole, 5-fluorocytosine and batrafen, have so far become available. It is exceptionally difficult to treat fungal infections medicinally, particularly because both the mycetes and the host cells are eukaryotic cells. For this reason, taking drugs which comprise the known antimycotic active substances is often associated with undesirable side-effects; for example, amphotericin B has a nephrotoxic effect. There is therefore a great need for pharmacologically active substances which can be used for producing medicaments which can be employed for treating mycoses, both prophylactically, when the immune system is impaired, and in the case of an infection which is already present. At the same time, the substances should display a specific action profile such that the growth and replication of the mycetes can be prevented selectively without concomitantly damaging the host organism.

There has to date been a lack of compatibile, informative test processes for identifying antimycotically active substances.

WO 95/11969 describes a process for screening antimycotic substances, in which process the effect of the substance to be tested is measured by its effect on the translation of a protein.

An object of the present invention is to develop a process for identifying antimycotically active substances, which process can be employed as universally as possible and enables a large number of potential active compounds to be tested in as efficient a manner as possible. An important feature of the process is that essential mycete genes are used as targets for the screening. This process differs from known processes in particular due to the fact that there is no requirement for any detailed knowledge of the biochemical function of the protein which is encoded by the essential gene.

The invention relates to a process for finding antimycotically active substances, which process employs essential mycete genes and/or the products of these essential genes as targets. In particular, antimycotically active substances are found as a result of the fact that they totally or partially inhibit the functional expression of the essential mycete genes (transcription and translation) or the functional activity of the encoded proteins.

The invention relates to a process for finding antimycotically active substances, in which process
a) a nucleic acid which controls the expression of an essential *Saccharomyces cerevisiae* protein and/or which encodes an essential *Saccharomyces cerevisiae* protein, or a part thereof, or the encoded essential protein itself, or
b) another nucleic acid which controls the expression of a protein which is derived from another mycete species and which is functionally similar to the protein mentioned under a) and/or encodes a protein which is derived from another mycete species and which is functionally similar to the protein mentioned under a), or the encoded functionally similar protein itself, is used as the target, with either
a) the effect of a substance to be investigated on the expression of the essential *Saccharomyces cerevisiae* protein or the functional activity of the encoded essential protein itself, or
b) the effect of a substance to be investigated on the expression of the functionally similar protein which is derived from another mycete species, or the functional activity of the encoded functionally similar protein itself, then being determined.

In one embodiment of the process, the nucleic acid is an essential gene or a part thereof, for example the promotor of the essential gene or an enhancer of the essential gene.

The invention involves identifying essential genes in mycetes, which genes can then be employed in the screening process.

The invention involves first of all identifying essential genes in *Saccharomyces cerevisiae*. The invention also involves using essential genes which have been identified in *Saccharomyces cerevisaie* (*S. cerevisiae*) to identify functionally similar genes in other mycetes. Where appropriate, these functionally similar genes can be essential genes in other mycetes.

In order to identify essential genes in *S. cerevisiae*, individual *S. cerevisiae* genes are removed from the *S. cerevisiae* genome by means of homologous recombination. The deletion is then lethal for the *S. cerevisiae* cells if the DNA segment which has been removed is an essential gene.

In order to produce appropriate deletions in the *S. cerevisiae* genome and to be able to select those *S. cerevisiae* cells which carry the deletion, use is made of a method in which the *S. cerevisiae* gene to be investigated is replaced by a marker gene. This marker gene (gene for a selection marker) can be used to select the cells in which a homologous recombination has taken place since, in these cells, the gene to be investigated has been replaced by the gene for the selection marker. Examples of selection markers which can be used are dominant selection markers or auxotrophic markers.

The auxotrophic markers used are genes which encode key enzymes of the amino acid or nucleobase synthetic pathways. For example, *S. cerevisiae* genes which encode enzymes from the amino acid metabolism of leucine (e.g. LEU2 gene), histidine (e.g. HIS3 gene) or tryptophan (e.g. TRP1 gene) or from the metabolism of the nucleobase uracil (e.g. URA3 gene) can be used as marker.

The process involves being able to use auxotrophic *S. cerevisiae* cells or strains, i.e. cells or strains in which the gene encoding the marker which is used in each case possesses one or more mutations thereby ensuring that no functionally active enzyme is expressed. These auxotrophic cells or strains are only able to grow in nutrient media which contain the corresponding amino acids or nucleobases. Examples of strains which can be used are all the *S. cerevisiae* laboratory strains which possess auxotrophic and/or nucleobase markers. If diploid *S. cerevisiae* cells or strains are used, the corresponding marker genes then have to be present in homozygously mutated form. Use is made, in particular, of the train CEN.PK2 (Scientific Research & Development GmbH, Oberursel, Germany) or isogenic derivatives of the strain.

The process also involves using *S. cerevisiae* cells or strains which do not possess any suitable auxotrophic markers, for example prototrophic S. cerevisiae cells or strains. Dominant selection markers, for example resistance genes such as the kanamycin resistance gene, can then be used as markers.

In order to achieve homologous recombination in which, in S. cerevisiae genes, the DNA sequence of the S. cerevisiae gene to be investigated is replaced totally or partly by the sequence of the marker gene, use is made of DNA fragments in which the marker gene is flanked, at its 5' and 3' ends, by sequences which are homologous with sequence segments at the 5' and 3' ends of the S. cerevisiae gene to be investigated.

A variety of methods, which are more or less equally well suited for deleting specific S. cerevisiae genes, are available for preparing appropriate DNA fragments. A linear DNA fragment is employed for the transformation into a suitable S. cerevisiae cell or strain. The homologous recombination integrates this fragment into the S. cerevisiae genome.

Three different methods can be used in the process:
1. "Classical method" for producing deletion cassettes (Rothstein, R. J. (1983) Methods in Enzymology Vol. 101, 202–211).
2. "Classical method" using the PCR technique ("modified classical method").
3. SFH (short flanking homology) PCR method (Wach, A. et al. (1994) Yeast 10: 1793–1808; Guldner, U. et al. (1996) Nucleic Acids Research 24: 2519–2524).

1. In the "classical method" for producing deletion cassettes in the S. cerevisiae genome, the gene to be investigated is either already present in a suitable vector or is integrated into such a vector. All pBR, pUC and pBluescript® derivatives can, for example, be used in this method. Appropriately selected restriction cleavage sites are, for example, used to remove the major portion of the sequence of the gene to be investigated from one of these vectors, in association with which, however, the 5' and 3' regions of the gene to be investigated remain in the vector. The gene for the chosen selection marker is then-integrated between these remaining regions.
2. In a modified form of this "classical method", use is made of the PCR technique. In this method, the regions of the S. cerevisiae gene to be investigated which are located at the 3' and 5' ends, respectively, of the coding sequence are amplified by means of the PCR technique. In this method, it is only the margin regions of the two ends of the gene to be investigated which are amplified, making it necessary to carry out two PCR reactions for each gene to be investigated, with the 5' end of the gene being amplified on one occasion and the 3' end being amplified on another occasion. The length of the amplified DNA segments of the margin regions depends, for example, on the restriction cleavage sites which are present in this region. As a rule, the amplified margin regions of the gene to be investigated are of from 50 to 5000 base pairs in length, with a length of between 500 and 1000 base pairs (bp) being particularly preferred.

S. cerevisiae genomic DNA can, for example, be used as the template for the PCR reaction. Wild-type genes or modified wild-type genes can be used as the template for the PCR reactions. The primer pairs (a sense primer and an antisense primer in each case) are constructed such that they correspond to sequence segments at the 3' and 5' ends, respectively, of the S. cerevisiae gene to be investigated. In particular, the primers are chosen such that it is possible to use suitable restriction cleavage sites to effect integration into the vector.

Derivatives of the pUC vector, the pBR vector and the pBluescript® vector can be used as the vectors. Vectors which already contain a gene encoding a selection marker are particularly suitable. Vectors which contain the genes for the selection markers HIS3, LEU2, TRP1 or URA3 can in particular be used for this purpose. For example, the plasmids pPK5/6 (SEQ ID NO. 18), pPK7/8 (SEQ ID NO. 19), pPK9/10 (SEQ ID. NO. 20) and pPK13/14 (SEQ ID NO. 21) can be used for this purpose. The nucleotide sequences of plasmids pPK5/6, pPK7/8, pPK9/10 and pPK13/14 are given in the sequence listing. The preparation of these plasmids is described in Examples 2 to 6.

The PCR-generated DNA segments of the S. cerevisiae gene to be investigated are integrated into the vector at the two ends of the gene which encodes the selection marker and is already present in the vector, such that, as in the "classical method", the selection marker employed is then flanked, at its two ends, by homologous DNA sequences of the gene to be investigated.

3. Since homologous recombination surprisingly proceeds very efficiently and precisely in S. cerevisiae, the length of the DNA segments which are homologous with the S. cerevisiae gene to be investigated and which flank the gene for the selection marker can, where appropriate, be made substantially shorter than in the case of the "modified classical method". The length of the flanking regions, which are homologous with the gene to be investigated, only need to be about 20–60 base pairs, particularly preferably 30–45 base pairs. A particular advantage of the SFH-PCR method is that elaborate cloning steps are dispensed with.

A PCR reaction is carried out on a DNA template which contains the gene for the selection marker to be employed, in association with which the primers which are used are constructed such that the DNA sequence of the sense primer is homologous with the 5' end of the sequence of the selection marker and, in addition, the primer possesses, at its 5' end, a region which is preferably 40 nucleotides in length and which corresponds to the sequence at the 5' end of the S. cerevisiae gene to be investigated. In an analogous manner, the antisense primer is constructed such that it is complementary to the 3' end of the sequence of the gene for the selection marker, with this primer at the same time containing, at its 5' end, a region which is likewise preferably 40 nucleotides in length and which corresponds to the sequence at the 3' end of the gene to be investigated.

Vectors which already contain the gene for an auxotrophic or selection marker are, for example, used for amplifying S. cerevisiae genes to be investigated by means of the SFH-PCR method. The plasmid pUG6 is in particular used as the template. This plasmid contains a loxP-KanMX-loxP cassette (Güldener, U. et al. (1996) Nucleic Acids Research 24: 2519–2524), i.e. a kanamycin resistance gene is flanked at each end by a loxP sequence (loxP-KanMX-loxP cassette). Using this cassette has the advantage that, after the loxP-KanMX-loxP cassette has been integrated at the gene locus at which the S. cerevisiae gene to be investigated was located, the kanamycin resistance gene can, where appropriate, be removed once again from the S. cerevisiae genome. This cap be done using the bacteriophage P1 Cre recombinase. The Cre recombinase recognizes the loxP sequences and removes the DNA lying between the two loxP sequences by means of a process of homologous recombination. This results in only one loxP sequence remaining and so-called marker recovery is achieved, i.e. the S. cerevisiae strain can once again be transformed with a loxP-KanMX-loxP cassette. This is particularly advantageous if two or more functionally homologous genes are to be deleted in order to obtain a lethal phenotype.

The SFH-PCR method uses primers, in the PCR reaction, which possess a region at their 3' ends which is preferably about 20 nucleotides in length and which is homologous with sequences to the left or to the right, respectively, of the loxP-KanMX-loxP cassette, with the primers in each case posssessing a region at their 5' ends which is preferably 40 nucleotides in length and which is homologous with sequence segments at the ends of the gene to be investigated.

All three methods result in linear deletion cassettes which contain the gene for a chosen selection marker which is flanked, at both ends, by homologous sequences of the gene to be investigated. These deletion cassettes are used for transforming diploid *S. cerevisiae* strains. The diploid *S. cerevisiae* strain CEN.PK2 (Scientific Research & Development GmbH, Oberursel, Germany) can, for example, be used for this purpose.

CEN.PK2 Mata/MAT α ura3-52/ura3-52/ura3-52 leu2-3, 112/leu2-3, 112 his3Δ1/his3Δ1 trp1-289/trp1-289 MAL2-8$^c$/MAL2-8$^c$ SUC2/SUC2

The strain CEN.PK2 is propagated and cultured using known methods (Gietz, R. D. et al. (1992) Nucleic Acids Research 8: 1425; Güldener, U. et al. (1996) Nucleic Acids Research 24: 2519–2524).

The cells of the *S. cerevisiae* strain employed are transformed with an appropriate quantity of the linear deletion cassette DNA using known methods (for example Sambrook et al. (1989) Molecular Cloning, A Laboratory Manual. Cold Spring Habor Laboratory Press). After that, the medium in which the cells are being cultured is exchanged for a new medium, a so-called selective medium, which does not contain the corresponding amino acid (for example histidine, leucine or tryptophan) or nucleobase (for example uracil) or, when a deletion cassette containing the kanamycin resistance gene is used, the cells are then cultured in media containing geniticin (G418®). Alternatively, the transformed cells can be plated out on agar plates which have been prepared using the appropriate medium. This results in selection of the transformant in which homologous recombination has taken place, since it is only these cells which are able to grow under the altered conditions.

However, in most cases, only one of the two copies of the gene to be investigated which are present in the double set of chromosomes is replaced by the deletion cassette DNA when a diploid *S. cerevisiae* cell or strain is transformed, which means that a heterozygous-diploid *S. cerevisiae* cell or a heterozygous-diploid *S. cerevisiae* mutant strain is formed in which one copy of the gene to be investigated is replaced with the gene of the selection marker while the other copy of the gene to be investigated is retained in the genome. This has the advantage that, if an essential gene is deleted in this way, the heterozygous-diploid cell or the *S. cerevisiae* mutant strain continues to remain viable as a result of the second copy of the essential gene still being present.

Where appropriate, correct integration of the deletion cassette DNA at the predetermined chromosomal gene locus (gene locus of the gene to be investigated) can be checked by means of a Southern blot analysis (Southern, E. M. (1975) J. Mol. Biol. 98: 503–517) or by means of diagnostic PCR analysis using specific primers (Güldener, U. et al. (1996) Nucleic Acids Research 24: 2519–2524).

The genetic segregation of individual diploid cells can be monitored by means of tetrad analysis. For this, known methods are used to stimulate diploid strains, in particular heterozygous-diploid mutant strains, to perform reductive division (meiosis), for example by means of nitrogen impoverishment on potassium acetate plates (Sherman, F. et al. (1986) Cold Spring Harbor Laboratory Press, Cold Spring Harbor, N.Y.; Guthrie, C. und Fink, G. R. (1991) Methods in Enzymology. Volume 194. Academic Press, San Diego, 3–21; Ausubel, F. M. et al. (1987) Current Protocols in Molecular Biology, John Wiley & Sons, Inc., Chapter 13). The meiosis results in asci containing four ascospores (segregants) which, after partial enzymic digestion of the ascus spore wall with zymolyase (Ausubel et al. (1987)) can be isolated individually using a micromanipulator (e.g. from SINGER). If, for example, a heterozygous-diploid mutant strain in which an essential gene in the double chromosome set has been replaced by homologous recombination is subjected to a tetrad analysis, only two segregants then survive, namely those segregants which still carry the essential gene. The other two segregants are not viable since these segregants lack the gene which is to be investigated and which in this case is essential.

In order to verify whether the genes which have been investigated in this manner are indeed essential or whether genes which are adjacent to the gene locus of the gene to be investigated and which may possibly be essential have been "damaged" by the homologous recombination, the heterozygous-diploid *S. cerevisiae* mutant strains are transformed with a centromer plasmid which contains the gene to be investigated. The transformants are subjected to a tetrad analysis. If four rather than two viable segregants are then once again obtained, the gene which is to be investigated and which is present in the centromer plasmid is able to complement the defect in the two non-viable haploid *S. cerevisiae* cells/mutant strains, thereby proving that the *S. cerevisiae* gene under investigation is essential.

The centromer plasmids used are preferably plasmids which are present in low copy number, for example in 1 or 2 copies per cell. For example, the plasmids pRS313, pRS314, pRS315 and pRS316 (Sikorski, R. S. and Hieter, P. (1989) Genetics 122: 19–27), or similar plasmids, can be used for this purpose. The genes to be investigated, and preferably their 5' - and 3'-non-coding regions as well, are then integrated into these plasmids.

The methods which have been described can be used to investigate individual *Saccharomyces cerivisae* genes whose DNA sequences are completely or partly known. The complete DNA sequence of the *S. cerevisiae* genome was published on the World Wide Web (WWW) on Apr. 24, 1996.

The following possibilities exist for obtaining DNA sequences of the *S. cerevisiae* genome by way of the WWW.
MIPS (Munich Information Centre of Protein Sequence)
   Address: speedy.mips.biochem .mpg.de/mips/yeast/yeast-genom.htmix
SGD (Saccharomyces Genome Database, Stanford)
   Address: genome-www.stanford.edu/Saccharomyces
YPD (Yeast Protein Database, Cold Spring Harbor)
   Address: www.prteome.com/YPDhome.html The complete DNA sequence of the *S. cerevisiae* genome is also available by way of FTP (file transfer protocol) in Europe (e.g. under the address: ftp.mips.embnet.org), in the USA (address: genome-ftp.stanford.edu) or in Japan (address: ftp.nig.ac.jp).

With the aid of this sequence information, it is possible to use the methods which have been described for determining whether each individual *Saccharomyces cerevisiae* gene is or is not essential for *S. cerevisiae*.

In this way, the following genes in the *S. cerevisiae* genome, i.e. YGRO46w, YGR048w, YGR060w, YJL074c, YJR136c, YJR141w, YBR167c, YPL252c, YPL242c, YOR119c, YPL235w, YOR110w, YNL182c, YOR206w, YJL054w, YJL039c, YNL258c, YNL245c, YNL038w, YNL251c, YNL256w, YNL260c, YIR012w, YLR86w, YLR076c, YLR100w, YIR010w, YIL003w, YBR102c, YOL010w, YKL013c, YKL018w and YLL003w, were identified as being essential.

Table 6 provides an overview of these essential genes and the information which is connected therewith. Column 1 lists the designations of the mutant strains which were generated (CEN.PK2 strains in which the essential gene was replaced with a marker gene), while column 2 lists the systematic gene names of the essential genes (names under which the corresponding DNA sequences are stored in databases), column 3 lists the selection markers which are used for preparing these strains, and columns 4 and 5 list the deleted nucleotides, and the amino acids corresponding to them, of the essential genes (position 1 serves as a reference point; position 1 is the A of the probable Start codon ATG of the open reading frame). To the extent that they are available, the gene names (column 6) and entries in databases (DB) (column 7) are also listed. Database entries with regard to the essential nature of the genes are in particular recorded in this column. For example, in the case of the YGR060w gene, it is recorded that this gene has previously been classified as being non-essential. Using the CEN.PK2 strain, it has now been found, surprisingly, that the YGR060w gene is essential after all. In addition to this, column 8 lists, insofar as it is available, additional information, for example with regard to the function of the genes which have been identified as being essential, or of the encoded proteins, and/or homologies/similarities with other genes or proteins.

The information given in Table 6 underlines the fact that, although the DNA sequences of the *S. cerivisae* genes (column 2) are known, hardly anything is so far known about the function or the characteristic properties of these genes or the encoded proteins, and that the essential function of these genes, or of the proteins encoded by these genes, was not previously known either.

The sequences of the genes which have been identified as being essential are available in gene databases, e.g. the abovementioned databases, under the systematic gene name (column 2 in Table 6). The invention relates to the use of the essential genes YGR046w, YGR048w, YGR060w, YJL074c, YJR136c, YJR141w, YBR167c, YPL252c, YPL242c, YOR119c, YPL235w, YOR110w, YNL182c, YOR206w, YJL054w, YJL039c, YNL258c, YNL245c, YNL038w, YNL251c, YNL256w, YNL260c, YIR012w, YLR086w, YLR076c, YLR100w, YIR010w, YIL003w, YBR102c, YOL010w, YKL013c, YKL018w and YLL003w.

The *Saccharomyces cerevisaie* strains specified in column 1 of Table 6, i.e. CEN.EN27, CEN.EN28, CEN.EN8, CEN.RO23, CEN.RO30, CEN.RO6, CEN.RO8, CEN.SR14, CEN.SR15, CEN.SR2, CEN.SR26, CEN.SR41, CEN.SR55, CEN.SR66, CEN.SR80, CEN.SR81, CEN.HE1, CEN.HE17, CEN.HE18, CEN.HE2, CEN.HE4, CEN.HE9, CEN.HI10, CEN.HI23, CEN.HI28, CEN.HI31, CEN.HI5, CEN.HI7, CEN.FE8, CEN.KR28, CEN.TS02, CEN.TS04 and CEN.ZI26, were generated from the strain CEN.PK2 (Scientific Research & Technologie GmbH, Oberursel, Germany) using one of the three abovementioned methods. These strains are defined by the fact that the nucleotides listed in column 4 of Table 6 (or the amino acids listed in column 5) were replaced by the selection markers listed in column 3 of Table 6.

The invention relates to the strains CEN.EN27, CEN.EN28, CEN.EN8, CEN.RO23, CEN.RO30, CEN.RO6, CEN.RO8, CEN.SR14, CEN.SR15, CEN.SR2, CEN.SR26, CEN.SR41, CEN.SR55, CEN.SR66, CEN.SR80, CEN.SR81, CEN.HE1, CEN.HE17, CEN.HE18, CEN.HE2, CEN.HE4, CEN.HE9, CEN.HI10, CEN.HI23, CEN.HI28, CEN.HI31, CEN.HI5, CEN.HI7, CEN.FE8, CEN.KR28, CEN.TS02, CEN.TS04 and CEN.ZI26, and to methods for preparing these strains and to the use of these strains.

One embodiment of the process is that the essential genes of *Saccharomyces cerevisiae*, in particular the genes YGR046w, YGR048w, YGR060w, YJL074c, YJR136c, YJR141w, YBR167c, YPL252c, YPL242c, YOR119c, YPL235w, YOR110w, YNL182c, YOR206w, YJL054w, YJL039c, YNL258c, YNL245c, YNL038w, YNL251c, YNL256w, YNL260c, YIR012w, YLR086w, YLR076c, YLR100w, YIR010w, YIL003w, YBR102c, YOL010w, YKL013c, YKL018w and YLL003w, or parts thereof, are used to identify corresponding genes, in particular sequentially similar and/or functionally similar genes, in other mycetes.

Sequentially homologous genes can be isolated from genomic libraries and/or cDNA libraries of the corresponding mycetes using known methods, e.g. by means of homology screening (Sambrook, J. et al. (1989) Molecular Cloning. Cold Spring Harbor Laboratory Press, N.Y.) or by means of the PCR technique using specific primers.

Functionally similar genes in other mycete species are genes which, in the other mycete species, have a function which is similar or identical to that of the essential genes which have been identified in *S. cerevisiae*. The functionally similar genes may, where appropriate, be functionally homologous to the corresponding *S. cerevisiae* genes. Functionally similar genes may, where appropriate, be sequentially homologous to the corresponding essential *S. cerevisiae* genes. Functionally similar or functionally homologous genes from other mycetes preferably encode proteins whose function is similar to that of the corresponding *S. cerevisiae* proteins (functionally similar proteins) or whose function is homologous with that of the corresponding *S. cerevisiae* proteins (functionally homologous proteins). Functionally similar or functionally homologous genes from other mycetes, or the proteins which are encoded by these genes, are able entirely or partially to complement the function of the corresponding essential *S. cerevisiae* gene or of the protein which is encoded by this gene.

The invention therefore also relates to methods by which genes which are functionally similar to the essential genes in *S. cerevisiae* can be identified in other mycetes. The invention relates, in particular, to methods for identifying functionally similar genes in other mycetes using the essential genes from *Saccharomyces cerevisiae*.

In these methods for identifying functionally similar genes in other mycetes, preference is given to generating *Saccharomyces cerevisaie* cells in which an essential *Saccharomyces cerevisaie* gene is placed under the control of a regulatable promoter. The *Saccharomyces cerevisaie* cells which have been altered in this way are then preferably propagated under growth conditions under which the regulatable promoter is active, and the altered *S. cerevisiae* cells are transformed with cDNA which was prepared from the other mycete species and which is present in an expression vector, after which the regulatable promoter is switched off, for example by means of altering the culture conditions, such that, in this way, those *Saccharomyces cerevisaie* cells are selected in which the cDNA encoding a functionally similar protein from the other mycete species is expressed.

The cDNA which represents the gene which is functionally similar to the essential *Saccharomyces cerevisaie* gene and which is derived from the other mycete species can then, where appropriate, be isolated from the selected *S. cerevisiae* cells and analyzed. In this way, the coding sequence of a functionally similar gene from another mycete species is available directly. The cDNA can be used to identify the functionally similar gene in the other mycete species by applying known methods, e.g. by means of screening a genomic library prepared from the other mycete species for homology. This then also makes the regulatory sequences, e.g. the promoter and enhancer, of the functionally similar gene available.

In such a method, one of the essential *Saccharomyces cerevisaie* genes, selected from the group of the genes YGR046w, YGR048w, YGR060w, YJL074c, YJR136c, YJR141w, YBR167c, YPl252c, YPL242c, YOR119c, YPL235w, YOR110w, YNL182c, YOR206w, YJL054w, YJL039c, YNL258c, YNL245c, YNL038w, YNL251c, YNL256w, YNL260c, YIR012w, YLR086w, YLR076c, YLR100w, YIR010w, YIL003w, YBR102c, YOL010w, YKL013c, YKL018w and YLL003w, is preferably placed under the control of a regulatable promoter.

For example, in order to find functionally similar genes in other mycetes, mRNA can be isolated by known methods (Sambrock et al., 1989) from a mycete species to be investigated, and cDNA can be prepared from the mRNA by means of methods which are likewise known (Sambrock et al., 1989; or cDNA synthesis kits, e.g. from Stratagene).

The cDNA which has been prepared can be integrated into a suitable expression vector in a directed manner.

For example, the first cDNA strand can be synthesized in the presence of primers which possess restriction cleavage sites which are suitable for permitting a subsequent cloning in the correct orientation in front of the relevant promoter of the expression vector. The restriction cleavage sites employed can be any known restriction cleavage sites. The primer employed can, for example, be the primer which is described below and which is approx. 50 nucleotides in length:
SEQ ID NO. 1: 5'-GAGAGAGAGAGAGAGAGAGAA CTAGTXXXXXXTTTTTTTTTTTTTTTTTT-3'
The sequence $(X)_6$ denotes a suitable restriction cleavage site, for example for XhoI.

After the second strand synthesis, the cohesive ends of the double-stranded cDNA can be filled in (making blunt ends), and the ends of the cDNA can then be ligated to suitable DNA adaptor sequences. The DNA adaptor sequences should contain a restriction cleavage site which should be different from the restriction cleavage site which was used in the primer for synthesizing the first cDNA strand. The DNA adaptor can, for example, be composed of 9-mer and 13-mer oligonucleotides which are complementary to each other and which, at their end, exhibit the cohesive end of a restriction cleavage site. For example, these ends can be an EcoRi cleavage site:
SEQ ID NO. 2: 5' XXXXXGGCACGAG 3' SEQ ID NO: 38 3' XCCGTGCTC 5'
The Xs in the depicted adaptor sequence constitute the cohesive end of a restriction cleavage site.

The cDNA, provided with appropriate adaptor sequences, is then cut with the restriction endonuclease, for example with XhoI, whose recognition site was used in the primer for synthesizing the first cDNA strand. In this example, the resulting cDNA would consequently have a XhoI protruding end at its 3' end and an EcoRI protruding end at its 5' end and could consequently be integrated in a directed manner into an expression vector which was cut with the restriction enzymes XhoI and EcoRI.

Suitable expression vectors are, inter alia, *E. coli/S. cerevisiae* shuttle vectors, i.e. vectors which can be used both for *E. coli* and for *S. cerevisiae*. Such vectors can then be replicated, for example, in *E. coli*. The expression vectors employed can be both those vectors which are present in high copy number in *S. cerevisiae* cells and those which are present in low copy number in these cells. For example, vectors from the pRS423–pRS426 series (pRS423, pRS424, pRS425, pRS426) or the pRS313–pRS316 series (pRS313, pRS314, pRS315, pRS316) (Sikorski, R. S. and Hieter P., (1989) Genetics 122: 19–27; Christianson, T. W. et al., (1992) Gene 110: 119–122) are suitable for this purpose.

The expression vectors should possess suitable *S. cerevisiae* promoters and terminators. If the expression vectors employed do not have these, appropriate promoters and terminators are then inserted in such a way that it still remains possible to subsequently incorporate the cDNA which is generated. The promoters of the *S. cerevisiae* genes MET25, PGK1, TPI1, TDH3, ADHI and URA3 are particularly suitable. Use can be made both of promoters of the wild-type genes, in unaltered form, and of promotors which have been altered in that particular activator sequences and/or repressor sequences have been removed. Examples of suitable terminators are the terminators of the *S. cerevisiae* genes MET25, PGK1, TPI1, TDH3, ADHI and URA3.

In methods for finding functionally similar genes in other mycete species, an essential *S. cerevisiae* gene is selected and this gene is placed either integratively (1) or extrachomosomally (2), under the control of a regulatable promoter.

1. In order to integrate a regulatable promoter into the *S. cerevisiae* genome, this promoter is exchanged for the native promoter of the selected essential gene, for example by means of PCR-mediated homologous recombination (Güldener et al., 1996). The PCR-mediated homologous recombination can, for example, be carried out in the diploid *S. cerevisiae* strain CEN.PK2. The genetic segregation can be checked by tetrad analysis.

In the tetrad analysis, four viable ascospores are obtained, with the selected essential gene being under the control of the native promoter in two haploid segregants and being under the control of the regulatable promoter in the other two segregants. The latter haploid segregants are used for transformation with the cDNA which is present in the expression vector.

2. In the extrachromosomal variant, the selected essential gene of *S. cerevisiae*, containing the cDNA which is present in the expression vector, is first of all inserted into a suitable expression vector, for example an *E. coli/S. cerevisiae* shuttle vector, downstream of a regulatable *S. cerevisiae* promoter. For example, the essential gene can, for this purpose, be amplified, from the ATG start codon up to and including the termination sequence, by means of PCR which is carried out on *S. cerevisiae* genomic DNA. The primers which are used for this can be constructed such that they contain recognition sites for suitable restriction enzymes, which sites facilitate subsequent insertion downstream of the regulatable promoter of an expression vector.

The recombinant expression vector, containing a plasmid-coded copy of the selected essential *S. cerevisiae* gene under the control of a regulatable promoter, is subsequently used for transcomplementing the corresponding mutant allele. The corresponding mutant allele can be selected from the heterozygous-diploid mutant strains which were prepared by homologous recombination and which are listed in Table 6 (column 1 in Table 6).

The expression vector containing the selected essential *S. cerevisiae* gene is transformed into the corresponding heterozygous-diploid mutant strain which carries the gene of a selection marker instead of the selected essential *S. cerevisiae* gene. The transformants are isolated by selecting for the auxotrophic or nucleobase marker which is present in the expression vector employed. The resulting transformed heterozygous-diploid mutant strains are subjected to a tetrad analysis. Four viable segregants are obtained in this analysis. By retracing the corresponding markers of the mutant allele and the expression vector, it is possible to distinguish transformed wild-type segregants from segregants in which the genomic copy of the essential gene has been removed. Segregants in which the genomic copy of the selected essential gene has been removed are termed trans-complemented haploid mutant strains. They are used for transformation with the cDNA which is present in the expression vector and which is derived from the mycete species to be investigated.

In particular, heterozygous-diploid *Saccharomyces cerevisaie* cells in which one of the essential genes is replaced by a marker gene are transformed with a recombinant expression vector which contains the coding part of the essential *Saccharomyces cerevisaie* gene under the control of a regulatable promoter. For example, an essential gene is replaced, in the heterozygous-diploid *Saccharomyces cerevisiae* cells, by a gene which encodes an auxotrophic marker or by a resistance gene.

In the process, preference is given to using *Saccharomyces cerevisaie* cells of the strain CEN.PK2. Preference is also given to using this strain to generate *Saccharomyces cerevisaie* cells in whose genome the native promoter of the essential gene is replaced by a regulatable promoter or such cells in which the native promoter of the essential gene is replaced extrachromosomally by a regulatable promoter.

The invention relates to the use of *Saccharomyces cerevisaie* cells of the strains CEN.EN27, CEN.EN28, CEN.EN8, CEN.RO23, CEN.RO30, CEN.RO6, CEN.RO8, CEN.SR14, CEN.SR15, CEN.SR2, CEN.SR26, CEN.SR41, CEN.SR55, CEN.SR66, CEN.SR80, CEN.SR81, CEN.HE1, CEN.HE17, CEN.HE18, CEN.HE2, CEN.HE4, CEN.HE9, CEN.HI10, CEN.HI23, CEN.HI28, CEN.HI31, CEN.HI5, CEN.HI7, CEN.FE8, CEN.KR28, CEN.TS02, CEN.TS04 and CEN.ZI26 in a method for identifying functionally similar genes and/or functionally similar proteins in other mycetes, in particular for identifying functionally similar genes in *Candida albicans* and *Aspargillus fumigatus*. In addition, the invention relates to the use of these *Saccharomyces cerevisaie* cells for identifying functionally similar human, animal or plant genes or proteins which are encoded by these genes (or for checking whether functionally similar human, animal or plant genes, or the proteins encoded by these genes, at all exist).

Regulatable promoters which can be employed are activatable and/or non-activatable or repressible promoters. These promoters can be composed of naturally and/or artificially arranged promoter sequences.

Examples of regulatable promoters which can be used are the promoters of the GAL1 gene and corresponding promoter derivatives, for example promoter derivatives in which various UAS (upstream activating sequence) elements have been removed (GALS, GALL; Mumberg, J. et al., (1994) Nucleic Acids Research 22: 5767–5768). Other regulatable promoters which can be used are the promoters of gluconeogenic genes, such as FBP1, PCK1 and ICL1, or parts thereof, for example their activator (UAS1 or UAS2) or repressor (URS, upstream repression sequence) sequences (Niederacher et al. (1992) Curr. Genet. 22: 363–370; Proft et al. (1995) Mol. Gen. Genet. 246: 367–373; Schülleretal., (1992) EMBO J. 11: 107–114; Guarente et al., (1984) Cell 36: 503–511).

The process involves a *S. cerevisiae* mutant strain which has been altered in this way (i.e. which contains a regulatable promoter) being propagated under growth conditions under which the regulatable promoter is active, such that the essential *S. cervisiae* gene is expressed. The *S. cerevisiae* cells are then transformed with a representative quantity of the recombinant expression vector which contains the cDNA of the mycete species to be investigated. The transformants then additionally express the protein whose cDNA is present in the recombinant expression vector.

The process involves the growth conditions being altered such that the regulatable promoter, under whose control the selected essential *S. cerevisiae* gene is expressed, is switched off. For example, the growth conditions can be altered by changing the medium. If, for example, the GAL1 promoter, or a derivative of this promoter is used, a change can be from a medium containing galactose (induced state) to a medium containing glucose (repressed state).

These altered conditions are lethal for *S. cerevisiae* cells in which the recombinant expression vector does not carry the cDNA of the functionally similar gene of the other mycete species (i.e. in which the function of the essential gene cannot be complemented by a functionally similar gene). By contrast, *S. cerevisiae* cells in which a functionally similar gene of the other mycete species is expressed are able to survive since these cells are able to complement the lethal metabolic defect with the protein which is encoded by the functionally similar gene.

The process involves isolating the expression vector (the plasmid) from the surviving transformants using known methods (Strathern, J. N. and Higgins, D. R. (1991) Recovery of Plasmids from Yeast into *Escherichia coli:* Shuttle Vectors in: Guthrie, C. and Fink, G. R. Methods in Enzymology. Volume 194. Guide to yeast genetics and molecular biology. Academic Press, San Diego, 319–329) and analyzing the cDNA using methods of DNA analysis, for example by means of DNA sequencing (Sanger et al., (1977) Proc. Natl. Acad. Sci. USA 74; 5463–5467).

The process involves essential *S. cerevisiae* genes being employed for identifying functionally similar and/or sequentially homologous genes in other mycetes, in particular genes of functionally similar and/or sequentially homologous mycetes which are pathogenic to humans, animals and plants. For example, mycetes of the classes Phycomycetes or Eumycetes, particularly of the subclasses Basidiomycetes and Ascomycetes, in particular Hemiascomycetales (yeasts) and Plectascales (mold) and Gymnascales (skin and hair fungi), or of the class Hyphomycetes, in particular of the subclasses Conidiosporales (skin fungi) and Thallosporales (budding fungi) can be used for this purpose, with the genera Mucor, Rhizopus, Coccidioides, Paracoccidioides (brasiliensis) (Blasomyces brasiliensis), Endomyces (Blastomyces), Aspergillus, Penicillium (Scopulariopsis), Trichophyton (Ctenomyces), Epidermophyton, Microsporon, Piedraia, Hormodendron, Phialophora, Sporotrichon, Cryptococcus, Candida, Geotrichum and Trichosporon being used, in particular. The use of *Candida albicans, Aspargillus fumigatus, Coccidioides immitis, Cryptococcus neoformans, Histoplasma capsulatum, Blasomyces dermatitidis, Paracoccidioides brasiliens* and *Sporothrix schenckii* is particularly to be emphasized.

The process involves employing essential genes from *Saccharomyces cerevisaie* and functionally similar genes from other mycetes to identify substances which are able to totally or partially inhibit the functional expression of these essential *S. cerevisiae* genes or of the functionally similar genes and/or the functional activity of the encoded proteins. Preferably, the functionally similar genes, or the proteins which are encoded by these genes, in the other mycetes are likewise essential. This process can be used to identify substances which inhibit the growth of mycetes and which can be employed as antimycotic agents, for example for producing pharmaceuticals.

A special feature of the process is that essential genes from *Saccharomyces cerevisiae* or functionally similar genes from other mycetes, in particular those genes which are essential for other mycete species, are employed as targets for screening the substances. The process involves being able to use the essential genes from *S. cerevisiae* and functionally similar and/or sequentially homologous essential *S. cerevisiae* genes from other mycetes as targets.

One embodiment of the process is that cells, in particular mycete cells which are overexpressing an essential gene which is employed as a target are prepared and that these cells are incubated with a substance to be tested. In this way, the growth-inhibiting effect of this substance can be determined in relation to the essential target gene. An individual gene which is investigated in this process is also termed the target gene or the gene to be investigated. A target gene can be an essential *S. cerevisiae* gene, in particular one of the genes YGR046w, YGR048w, YGR060w, YJL074c, YJR136c, YJR141w, YBR167c, YPL252c, YPL242c, YOR119c, YPL235w, YOR110w, YNL182c, YOR206w, YJL054w, YJL039c, YNL258c, YNL245c, YNL038w, YNL251c, YNL256w, YNL260c, YIR012w, YLR086w, YLR076c, YLR100w, YIR010w, YIL003w, YBR102c, YOL001w, YKL013c, YKL018w or YLL003w, or a functionally similar gene from another mycete species. In the process, the growth-inhibiting effect of a substance on a cell in which a target gene is being overexpressed is determined. In this context, the substance can either inhibit the expression of the essential gene or of the functionally similar gene and/or inhibit the functional activity of the encoded protein.

Another embodiment is that cells, in particular mycete cells, which are expressing a target gene to different extents are prepared and that these cells are then incubated with a substance to be tested and the growth-inhibiting effect of this substance on the cells is determined in a comparative manner.

The process involves using two or more cells, in particular mycete cells or strains derived therefrom, which differ from each other by the fact that they are expressing the target gene to differing extents. For example, two, three, four, five, ten or more cells, or the strains corresponding to them, can be analyzed comparatively with regard to the growth-inhibiting effect of a substance which is used at a defined concentration. Such concentration series can, for example, distinguish antimycotically active substances from cytotoxic or inactive substances.

One particular embodiment of the process is that haploid mycete cells/strains are used for the screening; it is in particular possible to use haploid *S. cerevisiae* cells/strains for this purpose.

The process involves integrating the essential gene which is selected as the target into a suitable expression vector.

*E. coli/S. cerevisiae* shuttle vectors are examples of suitable expression vectors. In particular, use can be made of vectors which differ in their number of copies per cell. For example, vectors can, on the one hand, be used which are present in transformed *S. cerevisiae* cells at a high copy number as can, on the other hand, those vectors which are present at low copy number. One embodiment employs expression vectors which allow the target gene to be integrated into the *S. cerevisiae* genome.

Examples of suitable expression vectors are the vectors pRS423, pRS424, pRS425, pRS426, pRS313, pRS314, pRS315, pRS316, pRS303, pRS304, pRS305, pRS306 (Sikorski and Hieter, 1989; Christianson, et al., 1992).

The vectors of the pRS423–pRS426 series are present at high copy number (about 50–100 copies/cell). By contrast, the vectors of the pRS313–pRS316 series are present at low copy number (1–2 copies/cell). If vectors from these two series are used, the target gene is then present as an extrachromosomal copy. The vectors of the pRS303–pRS306 series can be used to integrate the target genes into the genome. By means of using these three different types of expression vector, which only differ with regard to the number of copies at which they are present in *S. cerevisiae* cells, it is possible to achieve a differentiated or graded expression of the essential *S. cerevisiae* gene or the functionally similar gene, respectively.

The process involves determining, in a comparative manner, the growth-inhibiting effect of substances in relation to cells (e.g. mycete cells)/strains which are transformed with different expression vectors which differ, for example, in the number of copies of the vector/cell. Such cells are able to express the essential target gene to different extents and to exhibit a graded reaction to the substance.

The process also involves achieving varying levels of expression of the target gene in different cells, in particular mycete cells (controlled overexpression) by the target gene being inserted in expression vectors between especially selected promoters and terminators, for example *S. cerevisiae* promoters and terminators. For example, promoters of the *S. cerevisiae* gene which are expressed constitutively but at varying levels are suitable for this purpose. Examples of such promoters are the native promoters of the *S. cerevisiae* genes MET25, PGK1, TPI1, TDH3, ADHI, URA3 and TRP1, and also appropriate derivatives of these promoters, for example promoter derivatives which do not contain particular activator sequences and/or repressor sequences.

Regulatable promoters are also suitable for achieving controlled overexpression of the target gene. For example, the native promoters of the GALL genes, or appropriate derivatives of the promoters, e.g. those derivatives in which various UAS elements have been removed (GALS, GALL; Mumberg et al., (1994) Nucleic Acids Research 22: 5767–5768) and also promoters of gluconeogenic genes, e.g. the promoters FBP1, PCK1 and ICL1, or parts of these promoters, e.g. their activator (UAS1 or UAS2) or repressor (URS) sequences in appropriate non-activatable or repressible test promoters (Schüller et al., (1992) EMBO J. 11: 107–114; Guarente et al., (1984) Cell 36: 503–51 1; Niederacher et al. (1992) Curr. Genet. 22: 363–370; Proft et al. (1995) Mol. Gen. Genet. 246: 367–373;) can be employed.

The terminators in the expression vectors can, for example, be the terminator sequences of the *S. cerevisiae* genes MET25, PGK1, TPI1, TDH3, ADHI and URA3.

The process involves being able to prepare a series of expression vectors, which all contain the same target gene but which differ from each other in that they express the target gene to differing extents (at varying levels), by means of using suitably chosen types of expression vector and/or preparing suitable expression vectors, where appropriate using promoters of differing strength and/or promoters which are regulated in different ways. Using such series of expression vectors, it is possible to achieve a target gene expression which is finely graded in its strength. Such series of expression vectors can be used to prepare mycete cells/mycete strains which express the target gene to different extents.

The process involves transforming the expression vectors into haploid wild-type S. cerevisiae cells. The resulting cells/strains are propagated in liquid medium and incubated with differing concentrations of the substance to be investigated, and the effect of this substance on the growth behavior of the cells/strains, which express the target gene to differing extents, is analyzed in a comparative manner. The process also involves using, as a reference, haploid S. cerevisiae cells/strains which have been transformed with the relevant expression vector type without any target gene.

The process involves being able to screen substances in various media when using regulatable promoters, in particular when using the GAL1 promoter and its derivatives (GALS and GALL), since, under these conditions, the strength of expression can be markedly affected by the choice of the particular medium. For example the strength of expression of the GAL1 promoter decreases in the following manner: 2% galactose>1% galactose+1% glucose>2% glycerol>2% glucose.

The growth-inhibiting effect of substances which inhibit the growth of S. cerevisiae wild-type cells can be totally or partially neutralized by overexpression of the essential S. cerevisiae gene or the functionally similar gene from another mycete species.

The process also involves identifying functionally similar and/or sequentially homologous counterparts of the essential S. cerevisiae genes in humans, animals or plants. The corresponding human, animal or plant genes could likewise be employed as target genes in the process in order to check whether antimycotically active substances also have an effect on these target genes. This is a particular advantage of the process since it is possible, in this way, to identify substances which specifically inhibit the growth of mycetes (or of particular mycete species). Specific antimycotically active substances should have an effect which is either lower in comparison, or have no effect at all, on corresponding, functionally similar and/or sequentially homologous human, animal or plant genes, or the proteins which are encoded by these genes.

The process also involves the possibility of checking whether human, animal or plant genes which are functionally similar and/or sequentially homologous to the corresponding essential mycete genes do exist at all. This can be done, for example, by checking the homology of the identified essential mycete genes, or parts of these genes, with the human, animal or plant sequences/genes which are available in databases. In this way it is possible to select from the identified essential mycete genes, in advance and depending on the nature of the task, those genes for which no sequentially homologous and/or functionally similar genes exist in humans, for example. In this way, the process offers a multitude of possibilities for specifically identifying antimycotically active substances which then do not harm the human body, for example. For example, it is possible to identify substances which can be used for producing pharmaceuticals for treating mycoses or for prophylaxis when the immune system is impaired. For example, these substances can be employed, for example, for producing medicaments which are used for treating mycotic infections which occur, for example, in the course of HIV infection or Aids, or diseases such as diabetes. The process can also be employed to identify substances which can be used for producing fungicides, in particular for producing fungicides which are harmless to humans and animals. The process can also be employed to identify specific antimycotically active substances which can be used for preserving foodstuffs and bodycare substances, for example.

The process furthermore also offers the possibility of identifying antimycotically active substances which, in a quite specific manner, only inhibit the growth of particular mycete species since it is possible, in a first step, to use the process to check whether functionally similar genes exist at all in another mycete species. On the other hand, this process can also be employed to identify substances which are simultaneously active against a large number of mycete species ("broad spectrum antimycotics"), since it is possible to use the process to establish, in a first step, whether genes which are functionally similar to a gene which is essential in S. cerevisiae exist in as many other mycete species as possible (e.g. mycete species which are pathogenic to humans).

A particular advantage of the screening method is that it is sufficient to know that the genes employed are essential; no further information about the function of the essential genes, or the function of the encoded proteins, is required. This is advantageous, in particular, for using the essential genes of S. cerevisiae to identify functionally similar genes in other mycete species, since the DNA sequences of many of these genes are not available.

The following are particular advantages of the process:
  There is no requirement for any knowledge of the biochemical function of the essential S. cerevisiae gene. All genes whose sequences are totally or partly known can be examined to determine whether they are essential.
  The essential S. cerevisiae genes can be used to identify functionally similar genes from other mycete species, with it once again not being necessary for anything to be known about the biochemical function of these genes.
  In addition to this, the sequences of potential functionally similar genes from other mycete species do not have to be known. It is only the the sequences of identified functionally similar cDNAs or genes which are elucidated.
  In the process for finding antimycotically active substances, no distinction is made as to whether the substance inhibits the functional expression of the essential or functionally similar gene or whether it inhibits the functional activity of the encoded protein.

EXAMPLES

Example 1

The "Classical Method" for Producing Deletion Cassettes, as Described for YJR141w (Table 6)

Deleting the *S. cerevisiae* ORF YJR141w gene using the *S. Cerevisiae* HIS3 gene:

1) A 1.7 kb XbaI fragment (obtained either from genomic *S. cerevisiae* DNA or from a corresponding cosmid clone which contains the YJR141w gene) was cloned into a puC1 8 vector which had been linearized with the restriction enzyme XbaI.

2) The plasmid obtained from 1.) was next cut with the restriction enzyme BstEII and, after the protruding DNA ends had been filled in with the Klenow polymerase enzyme (Sambrook et al., 1989), the resulting linear DNA fragment was cut with the restriction enzyme ClaI. This resulted in a DNA fragment of 3.52 kb (kilobase pairs) in size and one of 0.87 kb in size.

3) The *S. cerevisiae* HIS3 gene is inserted, as a genomic 1.6 kb BamHI fragment, into the pBluescript IIKS+ vector (stratagene) which has been cut with the restriction enzyme BamHI, thereby creating the plasmid pMR240.

4) Plasmid pMR240 was next cut with the restriction enzyme XhoI and the protruding DNA ends were then filled in using Kienow polymerase. The linear DNA fragment was cut with the restriction enzyme ClaI. This resulted in a 1.36 kb DNA fragment which contained the *S. cerevisiae* HIS3 gene.

5) The 3.52 kb DNA fragment from 2.) was ligated to the 1.36 kb DNA fragment obtained from 4.), thereby producing the plasmid pRO6. An 870 Bp DNA segment of the coding region of YJR 141w was deleted from plasmid pRO6 and replaced with the selection marker HIS3.

6) Plasmid pRO6 was linearized with the restriction endonuclease PvuII and used for transforming *S. cerevisiae*.

At the same time, the effect of the substance can be tested on functionally similar human, animal and plant genes or the encoded proteins, or a check can be made as to whether functionally similar or sequentially homologous genes do exist at all.

Individual substances can in this way be efficiently tested for their specific activity.

Example 2

Constructing Plasmids for the SFH Method.

1) The vector pBluescript®II KS+ (stratagene; sequence available: Genbank® X52327) was used as the starting vector.

2) The pBluescript®II KS+ vector was linearized with the restriction enzyme NotI and the protruding ends were subsequently removed by incubating with mung bean 5'-3'exonuclease. The vector pKS+ΔNotI (pBluescript®II KS vector without the NotI restriction cleavage site) was prepared by religating the truncated DNA fragment.

3) The plasmid pKS+ΔNotI was cut with the restriction enzymes PstI and BamHI and the DNA oligonucleotide which was produced from the primer pair PK3/PK4 was ligated into the open plasmid. The plasmid pKS+new (SEQ ID. NO. 17) which was produced in this way contains the new restriction cleavage sites NotI, StuI, SfiI and NcoI between the PstI and BamHi restriction cleavage sites:

PstI-NotI-StuI-SfiI-NcoI-BamHI

```
SEQ ID NO. 3:    5'-GCGGCCGCAAGGCCTCCATGGCCG-3'                PK3

SEQ ID NO. 4:    5'-GATCCGGCCATGGAGGCCTTGCGGCCGCTGCA-3'        PK4
```

4) Plasmid pKS+new (SEQ ID. NO. 17) was used as the starting vector for preparing the plasmids pPK5/6 (SEQ ID NO. 18), pPK7/8 (SEQ ID NO. 19), pPK9/10 (SEQ ID NO. 20) and pPK13/14 (SEQ ID NO. 21). The genes for the appropriate amino acid/nucleobase/auxotrophic markers were amplified from the wild-type or modified wild-type genes by means of PCR and using suitable primers (Example 4 and Example 5).

Example 3

Constructing Plasmid pPK5/6 (pKS+New-HIS 3) (SEQ ID NO. 18)

The HIS3 gene was amplified from genomic *S. cerevisiae* DNA by PCR using the primers PK5 and PK6; it was then cut with the restriction enzymes BamHI and NotI and inserted into plasmid pKS+new which had been cut with BamHI and NotI. The underlined DNA segments of the primers correspond to the segments which correspond to the respective homologous sequences of the *S. cerevisiae* genes.

```
                        ..NotI..
SEQ ID NO. 5:  5'-ATCTGCAGCGGCCGCGTTTTAAGAGCTTGGTGAGCGC-3'     PK5
                  PstI
                      ....SfiI.....
SEQ ID NO. 6:  5'-ATGGATCCGGCCATGGAGGCCTCGTTCAGAATGACACGTAT-3' PK6
                  BamHI
```

Example 4

Constructing Plasmid pK7/8 (pKS+New-LEU2) (SEQ ID NO. 19)

The *S. cerevisiae* LEU2 gene was amplified by PcR from Ycplac111 vector DNA (Gietz, R. D. and Sugino, A. (1988) Gene 74: 527–534), acting as the template (modified wild-type gene), using the primers PK7 and PK8; the amplified DNA was then cut with the restriction enzymes BamHI and NotI and inserted into plasmid pKS+new which had been cut with BamHI and NotI.

```
                     ....SfiI.....
SEQ ID No. 7:  5'-ATGGATCCGGCCATGGAGGCCTGTGGGAATACTCAGGTATCG-3'    PK7
                   BamHI

..NotI..
SEQ ID NO. 8:  5'-ATCTGCAGCGGCCGCGTCTACCCTATGAACATATTCCATT-3'      PK8
                    PstI
```

Example 5

Constructing Plasmid pPK9/10 (pKS+New-URA3)
(SEQ ID NO. 20)

The *S. cerevisiae* URA3 gene was amplified by PCR from Ycplac33 vector DNA (Gietz, R. D. and Sugino, A. (1988) Gene 74: 527–534), acting as a template (modified wild-type gene), using primers PK9 and PK10; the amplified DNA was then cut with the restriction enzymes BamHI and NotI and inserted into plasmid pKS+new which had been cut with BamHI and NotI.

primers XSL-2N2 and G385-1 (cf. Item 4.). The amplified DNA was then cut with the restriction enzymes ClaI and EcoRI, and the resulting 508 Bp DNA fragment was ligated into plasmid pPK9/10, which had been cut previously with the restriction enzymes ClaI and EcoRI. The resulting plasmid was designated p119-58.

2) The 5' region of YGR046w was amplified from genomic *S. cerevisiae* DNA, acting as the template, using the primers G385-3 and X9R2 (cf. item 4.). The amplified DNA was then cut with the restriction enzymes BamHI and BglII and the resulting 1336 Bp fragment was inserted into plasmid p119-58, which had been previously cut with BamHI. The resulting plasmid was designated pEN27.

3) Plasmid pEN27 was used for transforming *S. cerevisiae* after having been linearized with the restriction enzymes SacI and Asp7 18.

4) Primers employed:

```
                      ..NotI..
SEQ ID NO. 9:   5'-ATCTGCAGCGGCCGCAAACATGAGAATTGGGTAATAACTG-3'     PK9
                     PstI

....SfiI.....
SEQ ID NO. 10:  5'-ATGGATCCGGCCATGGAGGCCTTCAAGAATTAGCTTTTCAATTCATC-3'  PK10
                    BamHI
```

Example 6

Constructing Plasmid pPK13/14 (pKS+New-TRP1)
(SEQ ID NO. 21)

The TRP1 gene was amplified by PCR from genomic *S. cerevisiae* DNA using the primers PK13 and PK14; the amplified DNA was then cut with the restriction enzymes BamHI and PstI and inserted into plasmid pKS+new which had been cut with BamHI and PstI.

```
                      ..NotI..
SEQ ID NO. 11:  5'-ATCTGCAGCGGCCGCATTTAATAGAACAGCATCG-3'           PK13
                     PstI

....SfiI....
SEQ ID NO. 12:  5'-ATGGATCCGGCCATGGAGGCCACACCGCATAGATCGGC-3'       PK14
                    BamHI
```

Example 7

"Classical Method" Using the PCR Technique
("Modified Classical Method"), as Described for
YGR046w 1) The 3' region of YGR046w was amplified from genomic *S. cerevisiae* DNA, acting as the template, using the

```
SEQ ID No. 13:
XSL-2N2         5'- AGG CAG ACT ACA ACT TAG G -3'

SEQ ID NO. 14:
G385-1          5'- CTG AAT TCG ATG AGG AGA AGC TAG T -3'

SEQ ID NO. 15:
X9R2            5'- CTT CAA ACG CTT GTT AAA TCT TG -3'

SEQ ID NO. 16:
G385-3          5'- CAG GAT CCG TAG ACC ATT TTC AGA A -3'
```

Example 8

S. cerevisiae strain CEN.PK2 cells were transformed according to known methods with in each case approx. 5 µg of a linear deletion cassette DNA (Gietz et al., 1992; G üldener et al., 1996). The transformation mixture was plated out on appropriate selective media.

When a deletion cassette containing the kanamycin resistance gene was used, the transformed cells were plated out on complete medium (YEPD) containing geniticin (G418®). When deletion cassettes containing so-called auxotrophic markers were used, the transformed cells were plated out on synthetic minimal media (SCD) which did not contain the appropriate amino acid (histidine, leucine or tryptophan) or nucleobase (uracil). This thereby selected for the transformant in which homologous recombination had taken place, since it was only these cells which were able to grow under the altered conditions.

TABLE 6

| Name of the strain generated | systematic gene name | Selection marker | Nucleotides deleted | Amino acids deleted | Name of the gene | DB entry | Comments |
|---|---|---|---|---|---|---|---|
| CEN.EN27 | YGR046w | URA3 | 18–1143 | 9–381 | ~ | | |
| CEN.EN28 | YGR048w | LEU2 | 73–1077 | 25–359 | UFD1 | YPD, no entry | ubiquitin fusion degradation protein |
| CEN.EN8 | YGR060w | HIS3 | (–)231–836 | (–)77–279 | ERG25 | viable, temperature-sensitive | C-4 sterol methyl oxidase |
| CEN.RO23 | YJL074c | HIS3 | 169–3114 | 56–1038 | ~ | | similarity to Emericella nidulans chromosome scaffold protein |
| CEN.RO30 | YJR136c | loxP-KanMX-loxP | 4–1236 | 2–421 | | | |
| CEN.RO6 | YJR141w | HIS3 | 27–891 | 10–297 | / | | |
| CEN.RO8 | YBR167c | HIS3 | 110–330 | 37–110 | / | | |
| CEN.SR14 | YPL252c | loxP-KanMX-loxP | 4–516 | 2–172 | | | similarity to adrenoxin and ferrrodoxin |
| CEN.SR15 | YPL242c | loxP-KanMX-loxP | 91–4485 | 31–1495 | | | |
| CEN.SR2 | YOR119c | loxP-KanMX-loxP | 4–1452 | 2–484 | RIO1 | YPD, no entry | similarity to C. elegans ZK632.3 protein; function unknown |
| CEN.SR26 | YPL235w | loxP-KanMX-loxP | 4–1413 | 2–471 | | | homology to hypothetical protein YDR190c |
| CEN.SR41 | YOR110w | LEU2 | 61–1197 | 21–399 | | | homology to hypothetical protein YNL108c |
| CEN.SR55 | YNL182c | loxP-KanMX-loxP | 4–1665 | 2–555 | | | |
| CEN.SR66 | YOR206w | loxP-KanMX-loxP | 73–2130 | 25–710 | | | homology to RAD4 (Frameshift) |
| CEN.SR80 | YJL054w | loxP-KanMX-loxP | 82–1352 | 28–450 | | | |
| CEN.SR81 | YJL039c | loxP-KanMX-loxP | 4–5049 | 2–1683 | | | similarity to HSP70 family |
| CEN.HE1 | YNL258c | TRP1 | | | | | |
| CEN.HE17 | YNL245c | loxP-KanMX-loxP | | | | | |
| CEN.HE18 | YNL038w | loxP-KanMX-loxP | | | | | probable membrane protein |
| CEN.HE2 | YNL251c | loxP-KanMX-loxP | | | NRD1 | | plays a role in sequence specific regulation of nuclear pre m-RNA abundance |
| CEN.HE4 | YNL256w | loxP-KanMX-loxP | | | | | similarity to bacterial dihydropteroate synthase |
| CEN.HE9 | YNL260c | loxP-KanMX-loxP | | | | | |
| CEN.HI10 | YIR012w | URA3 | | | | | beta transducin repeats |
| CEN.HI23 | YLR086w | loxP-KanMX-loxP | | | | | similarity to S. pombe cut3 protein |
| CEN.HI28 | YLR076c | loxP-KanMX-loxP | | | | | |
| CEN.HI31 | YLR100w | loxP-KanMX-loxP | | | | | |
| CEN.HI5 | YIR010w | URA3 | | | | | EF-hand calcium binding domain |
| CEN.HI7 | YIL003w | URA3 | | | | | similarity to E. coli MRP protein; ATPase |
| CEN.FE8 | YBR102c | URA3 | | | | | hypothetical membrane protein |
| CEN.KR28 | YOL010w | loxP-KanMX-loxP | | | | | homology to S. pombe SPAC12 g 12.06 c protein |
| CEN.TS02 | YKL013c | loxP-KanMX-loxP | | | | | strong similarity to unknown C. elegans protein |
| CEN.TS04 | YKL018w | loxP-KanMX-loxP | | | | | |
| CEN.ZI26 | YLL003w | LEU2 | | | "SFI1" | | protein of unknown function |

TABLE 7

Primers which were used for the PCR-mediated gene deletion:

```
SEQ ID NO.22:
YPL252c-S1      5'ATA GGC GCT TCT CGT ATC TAT ACT CAA CCC GCC CCC
                AAT GCA GCT GAA GCT TCG TAC GC 3'
SEQ ID NO.23:
YPL252c-S2      5'AAA TTG GGG GCA CAA ATG AGG GGT AAA AAT GCA GAC
                ATT AGC ATA GGC CAC TAG TGG ATC TG 3'
SEQ ID NO.24:
YPL242c-S1      5'TCT AAA TCG TTA TGT TGA AAA CCT AGG CAC CAA TGT
                GAC TCA GCT GAA GCT TCG TAC GC 3'
SEQ ID NO.25:
YPL242c-S2      5'CAG CTT TTG CCC AAT ATG CTC AAA ACC GAG TTA TCT
                ATT AGC ATA GGC CAC TAG TGG ATC TG 3'
SEQ ID NO.26:
YPL235w-S1      5'CAA GTT ACT TTG AAA GGA AAT AAA AAA AAT TGT CAG
                CAT GCA GCT GAA GCT TCG TAC GC 3'
SEQ ID NO.27:
YPL235w-S2      5'ATA TTT GAT GCA ATT TCT GCC TTA AAG TAC AAA ATG
                CTT AGC ATA GGC CAC TAG TGG ATC TG 3'
SEQ ID NO.28:
YNL182c-S1      5'AAT ATT CAT AAA ACA GGA TCT TTC AAG GGA CGA TAA
                AAT GCA GCT GAA GCT TCG TAC GC 3'
SEQ ID NO.29:
YNL182c-S2      5'TTC CTA TTT TAT TGT ACA AAA TGC GCG ACT ATT CCG
                TTT AGC ATA GGC CAC TAG TGG ATC TG 3'
SEQ ID NO.30:
YOR206w-S1      5'TCA ATC GAA GCA TTT GAA GCA TAC TCT AGA CCA AAG
                AAG ACA GCT GAA GCT TCG TAC GC 3'
SEQ ID NO.31:
YOR206w-S2      5'TTG AAT TCA AGA CAA AAA ATC AAA TCT TGC TGA GTT
                GTT AGC ATA GGC CAC TAG TGG ATC TG 3'
SEQ ID NO.32:
YJL054w-S1      5'GAA GCC TGG CTA TAC CAA TCC GGC TTT AAA AGC CCT
                TGG TCA GCT GAA GCT TCG TAC GC 3'
SEQ ID NO.33:
YJL054w-S2      5'CTT TAC CCT GTT TGA CCC AGT TCT GTG GCC AAT CTT
                TTT CGC ATA GGC CAC TAG TGG ATC TG 3'
SEQ ID NO.34:
YJL039c-S1      5'TTC CTA AAA GTA ATT CTT AAA AGT GAT AAT GAA TGA
                CTT ACA GCT GAA GCT TCG TAC GC 3'
SEQ ID NO.35:
YJL039c-S2      5'ACC TAG TTG AAA AGA TTT GTT CCG CAG ATA AGA AAA
                AAT GGC ATA GGC CAC TAG TGG ATC TG 3'
SEQ ID NO.36:
YOR119c-S1      5'CAC AGG GCC GCA TTA TTT CTT TGA TTT CGT TTT TTT
                CAC CCA GCT GAA GCT TCG TAC GC 3'
SEQ ID NO.37:
YOR119c-S2      5'GAT TTA GAG ATT CAA ACT CCG TTA TTT TTA GAA GGT
                CAT GGC ATA GGC CAC TAG TGG ATC TG 3'
```

What is claimed is:

1. A method for testing antimycotical activity of a substance, comprising:

overexpressing a *Saccharomyces cerevisiae* protein which is encoded by YGR046w, or a portion thereof, in one or more *Saccharomyces cerevisiae* cells;

incubating said one or more *Saccharomyces cerevisiae* cells with the substance; and determining the growth inhibiting effect of the substance on said *Saccharomyces cerevisiae* cells.

2. The method of claim 1, wherein in the overexpressing step, the plasmid pPK5/6 is used, said plasmid comprising SEQ ID NO: 18.

3. The method of claim 1, wherein in the overexpressing step, the plasmid pPK7/8 is used, said plasmid comprising SEQ ID NO: 19.

4. The method of claim 1, wherein in the overexpressing step, the plasmid pPK9/10 is used, said plasmid comprising SEQ ID NO: 20.

5. The method of claim 1, wherein in the overexpressing step, the plasmid pPK13/14 is used, said plasmid comprising SEQ ID NO: 21.

6. The method of claim 1, wherein the overexpressing is performed at different levels in at least two *Saccharomyces cerevisiae* cells and wherein the growth inhibiting effect of the substance is determined in a comparative manner.

7. The method of claim 1, wherein said one or more *Saccharomyces cerevisiae* cells are of the strain CEN.PK2.

8. The method of claim 1, wherein said one or more *Saccharomyces cerevisiae* cells are haploid *Saccharomyces cerevisiae* cells.

* * * * *